United States Patent [19]

Klotz

[11] 4,292,458
[45] Sep. 29, 1981

[54] PRODUCTION OF HYDROCARBONS FROM ALCOHOLS

[75] Inventor: Marvin R. Klotz, Batavia, Ill.

[73] Assignee: Standard Oil Company (Indiana), Chicago, Ill.

[21] Appl. No.: 182,691

[22] Filed: Aug. 29, 1980

Related U.S. Application Data

[63] Continuation of Ser. No. 897,360, Apr.18, 1978, which is a continuation-in-part of Ser. No. 733,267, Oct. 18, 1976, abandoned, Ser. No. 819,974, Jul. 28, 1977, abandoned, and Ser. No. 836,403, Sep. 26, 1977, abandoned, which is a continuation-in-part of Ser. No. 733,267, , abandoned.

[51] Int. Cl.³ .................. C07C 1/20; C07C 11/00; C07C 15/00
[52] U.S. Cl. .................. 585/469; 585/357; 585/640; 585/733
[58] Field of Search ............ 585/357, 469, 639, 640, 585/733; 252/432; 423/277

[56] References Cited

U.S. PATENT DOCUMENTS

| | | | |
|---|---|---|---|
| 3,702,886 | 11/1972 | Argaver et al. | 423/328 |
| 3,931,349 | 1/1976 | Kuo | 585/733 X |
| 3,941,871 | 3/1976 | Dwyer et al. | 423/328 X |
| 4,035,430 | 7/1977 | Dwyer et al. | 585/733 X |
| 4,049,573 | 9/1977 | Kaeding | 252/432 |
| 4,052,472 | 10/1977 | Givens et al. | 585/469 |
| 4,052,479 | 10/1977 | Chang et al. | 585/640 |
| 4,066,714 | 1/1978 | Rodewaid | 585/640 |

Primary Examiner—Edward J. Meros
Attorney, Agent, or Firm—James L. Wilson; William T. McClain; William H. Magidson

[57] ABSTRACT

A new crystalline borosilicate comprises a molecular sieve material having the following composition in terms of mole ratios of oxides:

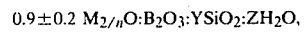

$$0.9 \pm 0.2\ M_{2/n}O:B_2O_3:YSiO_2:ZH_2O,$$

wherein M is at least one cation, n is the valence of the cation, Y is a value within the range of 4 to about 600, and Z is a value within the range of 0 to about 160, and providing a specific X-ray diffraction pattern. The borosilicate is used to catalyze various processes, such as isomerization, disproportionation, alkylation, transalkylation, and conversion of alcohols into gasoline-boiling-range products, olefins, and/or aromatics.

Broadly, there is provided a process for the conversion of an alcohol to useful hydrocarbon products, which process comprises contacting a feed comprising said alcohol under suitable conversion conditions with a catalyst comprising a crystalline borosilicate which comprises a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2\ M_{2/n}O:B_2O_3:YSiO_2:ZH_2O,$$

wherein M is at least one cation having a valence of n, Y is between 4 and about 600, and Z is between 0 and about 160.

50 Claims, No Drawings

PRODUCTION OF HYDROCARBONS FROM ALCOHOLS

CROSS REFERENCE TO RELATED APPLICATIONS

This application is a continuation-in-part application of co-pending application U.S. Ser. No. 897,360, filed in the United States Patent and Trademark Office on Apr. 18, 1978, said U.S. Ser. No. 897,360 being a continuation-in-part application of applications, U.S. Ser. No. 733,267, filed in the United States Patent and Trademark Office on Oct. 18, 1976, and now abandoned; U.S. Ser. No. 819,974, filed on July 28, 1977, and now abandoned; and U.S. Ser. No. 836,403, filed on Sept. 26, 1977, and now abandoned. U.S. Ser. No. 836,403 is, in turn, a continuation-in-part application of U.S. Ser. No. 733,267. Each of these applications is incorporated by reference herein and is made a part hereof, including but not limited to those portions of each which specifically appear hereinafter.

This application is being filed concurrently with two other applications. U.S. Ser. No. 182,796 is directed to borosilicates and claims their use as catalysts for hydrocarbon conversion processes and the isomerization of xylenes, while U.S. Ser. No. 182,792 is directed to borosilicates and claims their use as catalysts for the alkylation of benzene.

BACKGROUND OF THE INVENTION

1. Field of the Invention

This invention relates to novel crystalline borosilicates and to their use. More particularly, this invention relates to novel borosilicate crystalline molecular sieve materials having catalytic properties and to various hydrocarbon conversion processes using such crystalline borosilicates. Relevant patent art can be found in U.S. Patent Classes 423-326, 252-458 and 260-668.

2. Description of the Prior Art

Zeolitic materials, both natural and synthetic, have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

Relevant art is the above U.S. Pat. No. 3,702,886, in which Argauer, et al., disclose the crystalline aluminosilicate Zeolite ZSM-5 and the method for making the same. This patent teaches the production of a zeolite wherein aluminum or gallium oxides are present in the crystalline structure, along with silicon or germanium oxides. A specific ratio of the latter to the former are reacted to produce a class of zeolites designated ZSM-5, which is limited to crystalline alumino- or gallo-silicates or germanates and which has a specified X-ray diffraction pattern. The above ZSM-11 and ZSM-12 patents are similarly limited to crystalline alumino- or gallo-silicates or germanates, also having specified X-ray diffraction patterns.

As shown by Haag, et al., in U.S. Pat. No. 3,856,871, by Morrison, in U.S. Pat. No. 3,856,872, by Burress, in U.S. Pat. No. 3,856,873, and by Hayward, in U.S. Pat. No. 3,856,874, such ZSM-type aluminosilicates are used suitably for the isomerization of xylenes.

Manufacture of the ZSM materials utilizes a mixed base system in which sodium aluminate and a silicon-containing material are mixed together with sodium hydroxide and an organic base, such as tetrapropylammonium hydroxide and tetrapropylammonium bromide, under specified reaction conditions, to form the crystalline aluminosilicate.

Dwyer, et al., in U.S. Pat. No. 3,941,871 claim and teach an organosilicate having very little aluminum in its crystalline structure and possessing an X-ray diffraction pattern similar to the ZSM-5 composition. This patent is considered relevant art and was cited during the prosecution of one or more of the above-listed related applications.

Another relevant patent is U.S. Pat. No. 3,328,119, wherein Robson considers a synthetic crystalline aluminosilicate containing a minor amount of boria as an integral part of its crystal framework. This reference has been cited by the Examiner during the prosecution of one or more of the above-listed related applications.

Additional relevant art comprises U.S. Pat. Nos. 3,329,480; 3,329,481; 4,029,716; and 4,078,009. Young, in U.S. Pat. Nos. 3,329,480 and 3,329,481, discloses "zircono-silicates" and "titano-silicates", respectively. Keading, in U.S. Pat. Nos. 4,029,716 and 4,078,009, considers a crystalline aluminosilicate zeolite having a silica-to-alumina ratio of at least about 12 and a constraint index within the approximate range of 1 to 12, and having combined therewith boron in an amount of at least about 0.2 weight percent as a result of reaction of the zeolite with a boron-containing compound.

Chen, et al., in U.S. Pat. No. 4,148,835, consider a process for converting a feed containing a $C_1$–$C_4$ monohydric alcohol by contacting the feed, under conversion conditions, with a catalyst comprising a crystalline aluminosilicate zeolite, preferably a zeolite of the ZSM-type.

Keown, et al., in U.S. Pat. No. 3,751,504, disclose vapor-phase alkylation of aromatic hydrocarbons by contacting the aromatic hydrocarbons with an alkylating agent, in the vapor phase and in the presence of a catalyst comprising a crystalline aluminosilicate ZSM-5 zeolite.

Unland, et al., in U.S. Pat. Nos. 4,115,424 and 4,140,726 disclose an improved alkylation catalyst that comprises a crystalline aluminosilicate exemplified by a type X- or Y-zeolite, which catalyst includes potassium, rubidium, and/or cesium cations and contains boron and/or phosphorus. The aluminosilicates are modified to have the potassium, rubidium, and/or cesium cations and the boron and/or phosphorus present. The boron or phosphorus components can be incorporated by inclusion in an ion exchange solution, or by subsequently utilizing a solution of such component as a slurrying medium for catalyst particles or as an impregnating medium to be absorbed in the catalyst.

Plank, et al., in U.S. Pat. Nos. 3,140,249; 3,140,251; and 3,140,253, disclose the suspension of a molecular sieve material in a matrix of a refractory inorganic oxide and its distribution throughout said matrix. The preparation and use of cation-exchanged molecular sieves are considered.

Schwuger, et al., in U.S. Pat. No. 4,071,377, consider crystalline aluminosilicates and a crystalline borosilicate and their uses in a method of mechanical dishwashing. The Examiner considers this patent as relevant art and has cited it during the prosecution of U.S. Ser. No. 897,360.

The present invention is directed to catalysts that comprise AMS-1B crystalline borosilicates and their use as catalytic materials for the conversion of hydrocarbons.

SUMMARY OF THE INVENTION

Broadly, according to the present invention, there is provided a crystalline borosilicate which comprises a molecular sieve material having the following composition in terms of mole ratios of oxides:

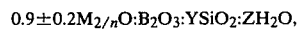

wherein M is at least one cation having a valence of n, Y is between 4 and about 600, and Z is between 0 and about 160.

Embodiments of such borosilicate provide an X-ray diffraction pattern comprising the following X-ray diffraction lines:

| d (Å) | Assigned Strength |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
| --- | --- |
| VW | less than 10 |
| W | 10-19 |
| M | 20-39 |
| MS | 40-70 |
| VS | greater than 70 | and "d" represents interplanar spacings, expressed in terms of Angstrom units. A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

There is provided a process for the conversion of a hydrocarbon stream, which process comprises contacting said stream at conversion conditions with a crystalline borosilicate which comprises a molecular sieve material having the following composition in terms of mole ratios of oxides:

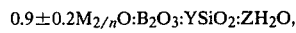

wherein M is at least one cation having a valence of n, Y is between 4 and about 600, and Z is between 0 and about 160, and providing an X-ray diffraction pattern comprising the following X-ray diffraction lines:

| d (Å) | Assigned Strength |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
| --- | --- |
| VW | less than 10 |
| W | 10-19 |
| M | 20-39 |
| MS | 40-70 |
| VS | greater than 70 |

In another embodiment, there is provided a process for the catalytic isomerization of an alkylaromatic having at least two alkyl groups, which process comprises contacting a feed comprising said alkylaromatic at isomerization conditions with a crystalline borosilicate which comprises a molecular sieve material having the following composition in terms of mole ratios of oxides:

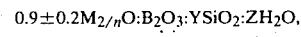

wherein M is at least one cation having a valence of n, Y is between 4 and about 600, and Z is between 0 and about 160, and providing an X-ray diffraction pattern comprising the following X-ray diffraction lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

A typical alkylaromatic is xylene.

In another embodiment of the present invention, there is provided a process for the alkylation of an aromatic hydrocarbon, which process comprises contacting a feed comprising said hydrocarbon under alkylation conditions and in the presence of an alkylating agent with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2 M_{2/n}O : B_2O_3 : YSiO_2 : ZH_2O,$$

wherein M is at least one cation having a valence of n, Y is about 4 to about 600, and Z is 0 to about 160.

In yet another embodiment of the present invention, there is provided a process for the conversion of an alcohol to useful hydrocarbons, which process comprises contacting a feed comprising said alcohol under suitable conversion conditions with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2 M_{2/n}O : B_2O_3 : YSiO_2 : ZH_2O,$$

wherein M is at least one cation having a valence of n, Y is about 4 to about 600, and Z is 0 to about 160.

The crystalline borosilicate of the present invention can be employed in various processes, some of which are reforming, hydrocracking, transalkylation, disproportionation, isomerization, and alkylation. They are particularly suitable for the isomerization of xylenes and conversion of ethylbenzene and they can be used to convert alcohols, such as methanol, to useful products, such as aromatics, olefins, or gasoline-boiling-range hydrocarbons.

DESCRIPTION AND SPECIFIC EMBODIMENTS

The present invention relates to novel synthetic crystalline molecular sieve materials, crystalline borosilicates. The family of such crystalline borosilicate materials, which are identified as AMS-1B borosilicates, has a particular X-ray diffraction pattern as is shown in the various tables hereinafter. Such crystalline borosilicate can generally be characterized, in terms of the mole ratios of oxides, as follows in Equation I:

$$0.9 \pm 0.2 M_{2/n}O : B_2O_3 : YSiO_2 : ZH_2O, \qquad (I)$$

wherein M is at least one cation, n is the valence of the cation, Y is between 4 and about 600, and Z representing the water present in such material is between 0 and about 160, or more.

In another instance, the claimed crystalline borosilicate can be represented in terms of mole ratios of oxides for the crystalline material not yet activated or calcined at a high temperature as follows in Equation II:

$$0.9 \pm 0.2 [WR_2O + [1 - W] M_{2/n}O] : B_2O_3 : YSiO_2 : ZH_2O, \qquad (II)$$

wherein R is an alkylammonium cation, M is at least one cation, n is the valence of the cation, Y is a value between 4 and about 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active metal cation, or mixtures thereof.

The expression "between 4 and about 600" for Y can be read as "within the range of 4 to about 600" and includes the value of "4". In a like manner for Z, the expression "between 0 and about 160" can be read as "within the range of 0 to about 160" and includes the value of "0".

Advantageously, the value for Y falls within the range of 4 to about 500. Suitably, Y is 4 to about 300; and preferably, about 50 to about 160. In Ser. No. 897,360, a more preferred range of about 80 to about 120 was taught. However, a preferred range of about 30 to about 160 and a more preferred range of about 40 to about 120 are more appropriate.

Suitably, Z is within the range of 0 to about 40.

The original cation "M" in the above formulations can be replaced in accordance with techniques well-known in the art, at least in part, by ion-exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically-active especially for hydrocarbon conversion. These materials include hydrogen, rare earth metals, aluminum, metals of Groups IB, IIB and VIII of the Periodic Table, noble metals, manganese, etc., and other catalytically-active materials and metals known to the art. The Periodic Table of Elements consulted was the Periodic Table found in the back of ADVANCED INORGANIC CHEMISTRY, F. Albert Cotton and Geoffrey Wilkinson, Interscience Publishers, a Division of John Wiley & Sons, New York, N.Y., U.S.A. (1972). The catalytically-active components can be present anywhere from about 0.0005 to about 15 weight percent of the AMS-1B crystalline borosilicate.

Members of the family of AMS-1B crystalline borosilicates possess a specified and distinguishing crystalline structure. Two methods were employed to obtain X-ray diffraction patterns of various samples of AMS-1B crystalline borosilicates.

In the first method, identified hereinafter as Method No. 1, a Phillips instrument which utilized copper K alpha radiation was employed. The theta angles were recorded on a strip chart using a proportional counter. The theta values recorded were converted to interplanar spacing values in Angstroms (Å) using the Bragg equation. The relative intensities (relative peak heights) were calculated as (100 I/Io), where Io is the intensity of the strongest recorded peak and I is the value actually read for the particular interplanar spacing.

In the second method, identified hereinafter as Method No. 2, the X-ray diffractometer was a Phillips instrument which utilized copper K alpha radiation in conjunction with an AMR focusing monochromometer and a theta compensating slit, in which its aperture varies with the theta angle. The output from the diffractometer was processed through a Canberra hardware/software package and reported by way of a strip chart and tabular printout. The compensating slit and the Canberra package tend to increase the peak/background ratios while reducing the peak intensities at low theta angles [large interplanar spacings] and increasing the peak intensities at high theta angles [small interplanar spacings].

For ease of reporting the results obtained by either method, the relative intensities (relative peak heights) were arbitrarily assigned the following values:

| Relative Peak Height | Assigned Strength |
|---|---|
| less than 10 | VW (very weak) |
| 10–19 | W (weak) |
| 20–39 | M (medium) |
| 40–70 | MS (medium strong) |
| greater than 70 | VS (very strong) |

These assigned strengths are used throughout this application.

An X-ray diffraction pattern obtained by means of Method No. 1 and displaying the significant lines in the indicated relative intensities (relative peak heights) and assigned strength for the AMS-1B crystalline borosilicates is presented in Table I hereinbelow:

TABLE I

| d (Å) | Relative Intensity (I/Io) | Assigned Strength |
|---|---|---|
| 11.04 ± 0.2 | 100 | VS |
| 10.04 ± 0.2 | 68 | MS |
| 7.37 ± 0.15 | 2 | VW |
| 6.70 ± 0.1 | 7 | VW |
| 6.32 ± 0.1 | 10 | W |
| 5.98 ± 0.07 | 20 | M |
| 5.68 ± 0.07 | 10 | W |
| 5.53 ± 0.05 | 13 | W |
| 5.30 ± 0.05 | 3 | VW |
| 5.21 ± 0.05 | 3 | VW |
| 4.98 ± 0.05 | 9 | VW |
| 4.62 ± 0.05 | 3 | VW |
| 4.37 ± 0.05 | 5 | VW |
| 4.27 ± 0.05 | 10 | W |
| 4.07 ± 0.05 | 2 | VW |
| 4.00 ± 0.05 | 6 | VW |
| 3.83 ± 0.05 | 84 | VS |
| 3.72 ± 0.05 | 48 | MS |
| 3.64 ± 0.05 | 23 | M |
| 3.42 ± 0.05 | 9 | VW |
| 3.30 ± 0.05 | 11 | W |
| 3.23 ± 0.05 | 3 | VW |
| 3.16 ± 0.05 | 2 | VW |
| 3.12 ± 0.05 | 2 | VW |
| 3.04 ± 0.05 | 9 | VW |
| 2.98 ± 0.02 | 16 | W |
| 2.94 ± 0.02 | 10 | W |
| 2.86 ± 0.02 | 2 | VW |
| 2.83 ± 0.02 | 1 | VW |
| 2.73 ± 0.02 | 3 | VW |
| 2.59 ± 0.02 | 3 | VW |
| 2.55 ± 0.02 | 3 | VW |
| 2.51 ± 0.02 | 3 | VW |
| 2.48 ± 0.02 | 5 | VW |
| 2.45 ± 0.02 | 3 | VW |
| 2.39 ± 0.02 | 5 | VW |
| 2.00 ± 0.02 | 13 | W |
| 1.99 ± 0.02 | 14 | W |
| 1.94 ± 0.02 | 6 | VW |
| 1.91 ± 0.02 | 4 | VW |
| 1.86 ± 0.02 | 2 | VW |
| 1.81 ± 0.02 | 1 | VW |
| 1.75 ± 0.02 | 2 | VW |
| 1.66 ± 0.02 | 4 | VW |
| 1.56 ± 0.02 | 2 | VW |

When Method No. 1 is employed, the above X-ray pattern is characteristic of the AMS-1B crystalline borosilicate having the oxide mole formula described in Equation I, which borosilicate has been calcined at 1,100° F. (593° C.) and wherein the tetraalkylammonium ion has been removed from the system by the calcination procedure.

In the following Table, the more significant interplanar spacings, d, and their assigned strengths are summarized from Table I above:

TABLE II

| d (Å) | Assigned Strength |
|---|---|
| 11.04 ± 0.2 | VS |
| 10.04 ± 0.2 | MS |
| 5.98 ± 0.07 | M |
| 3.83 ± 0.05 | VS |
| 3.72 ± 0.05 | MS |
| 3.64 ± 0.05 | M |

In instances in which the AMS-1B crystalline borosilicate in an as-produced state (prior to high temperature calcination, but after some reasonable amount of drying has taken place), is analyzed by X-ray diffraction analysis by Method No. 1, the crystalline borosilicate generally is characterized by Equation II above and has an X-ray diffraction pattern showing the following significant lines:

TABLE III

| d (Å) | Assigned Strength |
|---|---|
| 11.04 ± 0.2 | MS |
| 9.82 ± 0.2 | MS |
| 9.60 ± 0.2 | MW |
| 8.84 ± 0.2 | VW |
| 7.37 ± 0.2 | W |
| 7.02 ± 0.15 | VW |
| 6.60 ± 0.1 | VW |
| 6.32 ± 0.1 | W |
| 5.90 ± 0.07 | W |
| 5.68 ± 0.07 | W |
| 5.53 ± 0.05 | W |
| 5.27 ± 0.05 | VW |
| 5.09 ± 0.05 | VW |
| 4.95 ± 0.05 | W |
| 4.57 ± 0.05 | W |
| 4.44 ± 0.05 | VW |
| 4.35 ± 0.05 | W |
| 4.23 ± 0.05 | W |
| 4.04 ± 0.05 | VW |
| 3.97 ± 0.05 | W |
| 3.80 ± 0.05 | VS |
| 3.72 ± 0.05 | M |
| 3.67 ± 0.05 | MS |
| 3.60 ± 0.05 | MS |
| 3.45 ± 0.05 | VW |
| 3.41 ± 0.05 | W |
| 3.30 ± 0.05 | W |
| 3.28 ± 0.05 | W |
| 3.23 ± 0.05 | VW |
| 3.16 ± 0.05 | VW |
| 3.12 ± 0.05 | VW |
| 3.06 ± 0.05 | W |
| 2.96 ± 0.02 | W |
| 2.94 ± 0.02 | W |
| 2.85 ± 0.02 | VW |
| 2.76 ± 0.02 | VW |
| 2.71 ± 0.02 | W |
| 2.59 ± 0.02 | W |
| 2.56 ± 0.02 | VW |
| 2.49 ± 0.02 | VW |
| 2.47 ± 0.02 | W |
| 2.40 ± 0.02 | VW |
| 2.38 ± 0.02 | W |
| 2.33 ± 0.02 | VW |
| 2.31 ± 0.02 | VW |
| 2.28 ± 0.02 | VW |
| 2.21 ± 0.02 | VW |
| 2.19 ± 0.02 | VW |
| 2.16 ± 0.02 | VW |
| 2.10 ± 0.02 | VW |
| 2.06 ± 0.02 | VW |
| 2.00 ± 0.02 | W |
| 1.99 ± 0.02 | W |
| 1.94 ± 0.02 | W |
| 1.90 ± 0.02 | W |
| 1.86 ± 0.02 | W |
| 1.82 ± 0.02 | VW |
| 1.75 ± 0.02 | W |
| 1.71 ± 0.02 | VW |
| 1.66 ± 0.02 | W |

In the following Table, the more significant interplanar spacings, d, and their assigned strengths are summarized from Table III.

TABLE IV

| d (Å) | Assigned Strength |
|---|---|
| 11.04 ± 0.2 | MS |
| 9.82 ± 0.2 | MS |
| 3.80 ± 0.05 | VS |
| 3.72 ± 0.05 | M |
| 3.67 ± 0.05 | MS |
| 3.60 ± 0.05 | MS |

A typical X-ray diffraction pattern obtained by means of Method No. 2 and displaying the significant lines which have relative intensities (relative peak heights) of 11 or higher for an AMS-1B crystalline borosilicate after calcination at 1,000° F. (538° C.) is shown in Table V hereinbelow.

TABLE V

| d (Å) | Relative Intensity | Assigned Strength |
|---|---|---|
| 11.3 ± 0.2 | 38 | M |
| 10.1 ± 0.2 | 30 | M |
| 6.01 ± 0.07 | 14 | W |
| 4.35 ± 0.05 | 11 | W |
| 4.26 ± 0.05 | 14 | W |
| 3.84 ± 0.05 | 100 | VS |
| 3.72 ± 0.05 | 52 | MS |
| 3.65 ± 0.05 | 31 | M |
| 3.44 ± 0.05 | 14 | W |
| 3.33 ± 0.05 | 16 | W |
| 3.04 ± 0.05 | 16 | W |
| 2.97 ± 0.02 | 22 | M |
| 2.48 ± 0.02 | 11 | W |
| 1.99 ± 0.02 | 20 | M |
| 1.66 ± 0.02 | 12 | W |

An AMS-1B borosilicate which has been only subjected to mild drying at 165° C. (as-produced material) possesses an X-ray diffraction pattern obtained by Method No. 2, which pattern has the following significant lines:

TABLE VI

| d (Å) | Relative Intensity | Assigned Strength |
|---|---|---|
| 11.4 ± 0.2 | 19 | W |
| 10.1 ± 0.2 | 17 | W |
| 3.84 ± 0.05 | 100 | VS |
| 3.73 ± 0.05 | 43 | MS |
| 3.66 ± 0.05 | 26 | M |
| 3.45 ± 0.05 | 11 | W |
| 3.32 ± 0.05 | 13 | W |
| 3.05 ± 0.05 | 12 | W |
| 2.98 ± 0.02 | 16 | W |
| 1.99 ± 0.02 | 10 | W |
| 1.66 ± 0.02 | 20 | M |

The strip chart recordings of the calcined borosilicate reported in Table V above showed that this material had the following X-ray diffraction lines:

TABLE VII

| Interplanar Spacings, d (Å) | |
|---|---|
| Run 1 | Run 2* |
| 11.3 | 11.2 |
| 10.2 | 10.0 |
| 7.49 | 7.37 |
| 6.70 | 6.70 |
| 6.41 | 6.36 |
| 6.02 | 5.98 |
| 5.71 | 5.67 |
| 5.60 | 5.57 |
| 5.01 | 5.34 |
| 4.62 | 5.01 |
| 4.37 | 4.62 |
| 4.27 | 4.35 |
| 4.00 | 4.25 |
| 3.85 | 4.00 |
| 3.72 | 3.85 |
| 3.64 | 3.70 |
| 3.48 | 3.64 |
| 3.44 | 3.46 |
| 3.30 | 3.42 |
| 3.14 | 3.30 |
| 3.04 | 3.25 |
| 2.98 | 3.12 |
| 2.86 | 3.04 |
| 2.71 | 2.97 |
| 2.60 | 2.86 |

TABLE VII-continued

| Interplanar Spacings, d (Å) | |
|---|---|
| Run 1 | Run 2* |
| 2.48 | 2.71 |
| 2.39 | |
| 2.32 | |
| 2.22 | |
| 2.00 | |
| 1.99 | |
| 1.95 | |
| 1.91 | |
| 1.86 | |
| 1.75 | |
| 1.66 | |

*This run was terminated at a "d" of 2.71Å.

The AMS-1B crystalline borosilicates of the present invention are useful as catalysts for various hydrocarbon conversion processes and they are suitable for chemical absorption. Some of the hydrocarbon conversion processes for which the borosilicates appear to have relatively useful catalytic properties are fluidized catalytic cracking; hydrocracking; the isomerization of normal paraffins and naphthenes; the reforming of naphthas and gasoline-boiling-range feedstocks; the isomerization of aromatics, especially the isomerization of alkylaromatics, such as xylenes; the disproportionation of aromatics, such as toluene, to form mixtures of other more valuable products including benzene, xylene, and other higher methyl substituted benzenes; hydrotreating; alkylation; hydrodealkylation; hydrodesulfurization; and hydrodenitrogenation. They are particularly suitable for the isomerization of alkylaromatics, such as xylenes, and for the conversion of ethylbenzene. The AMS-1B borosilicates, in certain ion-exchanged forms, can be used to convert alcohols, such as methanol, to useful products, such as aromatics, olefins, or gasoline-boiling-range hydrocarbons.

When the AMS-1B crystalline borosilicate is used as a hydrocracking catalyst, hydrocracking charge stocks can pass over the catalyst at temperatures anywhere from about 500° F. (260° C.) to about 850° F. (454° C.) or higher using known molar ratios of hydrocarbon to hydrogen and varying pressures anywhere from a few up to many thousands of pounds per square inch or higher. The weight hourly space velocity and other process parameters can be varied consistent with the well-known teachings of the art.

The specified AMS-1B crystalline borosilicate is also suitable as a reforming catalyst to be used with the appropriate hydrogenation components at well-known reforming conditions including temperatures of anywhere from about 500° F. (260° C.) to 1,050° F. (566° C.), or more, pressures anywhere from a few up to 300 psig (2,169 kPa) to 1,000 psig (6,990 kPa), and weight hourly space velocities and hydrogen-to-hydrocarbon mole ratios consistent with those well known in the reforming art.

The present composition is also suitable for hydrocarbon isomerization and disproportionation. It is especially useful for liquid or vapor phase isomerization of xylenes and especially the isomerization of mixed xylenes to a near thermodynamic equilibrium concentration of paraxylene in the product. Operating conditions for the isomerization of a xylene feed broadly comprise a temperature of about 200° F. (93° C.) to about 1,000° F. (538° C.), a hydrogen-to-hydrocarbon mole ratio of about 0 to about 20, a weight hourly space velocity (WHSV) of about 0.01 weight unit of feed per hour per weight unit of catalyst ($hr^{-1}$) to about 90 $hr^{-1}$, and a pressure of about 0 psig (101.3 kPa) to about 1,000 psig (6,990 kPa). Advantageously, the conditions comprise a temperature of about 400° F. (204° C.) to about 900° F. (482° C.), a hydrogen-to-hydrocarbon mole ratio of about 1 to about 12, and a WHSV of about 1 $hr^{-1}$ to about 20 $hr^{-1}$, and a pressure of about 10 psig (170 kPa) to about 500 psig (3,547 kPa). The preferred conditions for the isomerization of xylenes comprise a temperature of about 600° F. (316° C.) to about 850° F. (454° C.), a hydrogen-to-hydrocarbon mole ratio of about 2 to about 8, a WHSV of about 1 $hr^{-1}$ to about 10 $hr^{-1}$, and a pressure of about 100 psig (790 kPa) to about 300 psig (2,169 kPa). The choice of catalytically-active metals to be placed on the AMS-1B crystalline borosilicate can be selected from any of those well known in the art. Nickel and molybdenum seem to be especially appropriate for isomerization of substituted aromatics. When used as a catalyst in isomerization processes with suitable cations placed on the ion-exchangeable sites within the AMS-1B crystalline borosilicate, reasonably high selectivities for production of desired isomers are obtained.

The crystalline borosilicates are suitable catalysts for the disproportionation of aromatics, as exemplified by the disproportionation of ethylbenzene to benzene and diethylbenzene.

The present crystalline borosilicates are suitable as catalytic materials for the alkylation of hydrocarbons. Hence, a catalytic composition comprising a crystalline borosilicate can be employed as a catalyst for the alkylation of benzene with a suitable alkylating agent. Appropriate alkylation conditions comprise an inlet temperature within the range of about 600° F. (316° C.) to about 900° F. (482° C.), a pressure within the range of about 0 psig (101.3 kPa) to about 2,000 psig (13,900 kPa), a WHSV with respect to benzene within the range of about 0.1 $hr^{-1}$ to about 450 $hr^{-1}$, a WHSV with respect to alkylating agent, e.g, ethylene, within the range of about 0.01 $hr^{-1}$ to about 20 $hr^{-1}$, a mole ratio of benzene to alkylating agent within the range of about 1 to about 60, a concentration of alkylating agent in inert gases within the range of about 1% to about 100%, an amount of crystalline borosilicate in the catalyst within the range of about 3 wt% to about 100 wt%, and a number of stages being employed in the reaction zone within the range of about 1 to about 10. Advantageously, the alkylation conditions comprise an inlet temperature within the range of about 650° F. (343° C.) to about 850° F. (454° C.), a pressure within the range of about 50 psig (446 kPa) to about 1,000 psig (6,990 kPa), a WHSV with respect to benzene within the range of 0.5 $hr^{-1}$ to about 300 $hr^{-1}$, a WHSV with respect to the alkylating agent within the range of about 0.2 $hr^{-1}$ to about 10 $hr^{-1}$, a mole ratio of benzene to alkylating agent within the range of about 5 to about 50, a concentration of alkylating agent in inert gases within the range of about 5% to about 65%, the amount of crystalline borosilicate in the catalyst within the range of about 5 wt% to about 80 wt%, and the number of stages being employed in the reaction zone within the range of about 2 to about 8. Preferably the alkylation conditions comprise an inlet temperature within the range of about 775° F. (413° C.) to about 800° F. (427° C.), a pressure within the range of about 150 psig (1,130 kPa) to about 450 psig (3,200 kPa), a WHSV with respect to benzene within the range of about 1.0 $hr^{-1}$ to about 200 $hr^{-1}$, a WHSV with respect to the alkylation agent within the range of about 0.2 $hr^{-1}$ to about 1.5 $hr^{-1}$, a mole ratio of benzene to alkylating agent within the range of about 10 to about 30, a concentration of alkylating agent in inert gases within the range of about 10% to about 30%, an amount of borosilicate in the catalyst within the range of about 10 wt% to about 70 wt%, and a number of stages within the reaction zone within the range of about 3 to about 7.

The above WHSV's based upon benzene (aromatics) and the above WHSV's based upon alkylating agent are WHSV's with respect to the total catalyst which contains a certain percentage of molecular sieve in the matrix material. The equivalent WHSV's based upon molecular sieve alone is the WHSV based upon total catalyst divided by the fraction of sieve in the catalyst. For example, for a catalyst containing 15% molecular sieve, the WHSV based upon the total catalyst must be divided by 0.15 to provide the WHSV based upon the sieve alone.

Various alkylating agents may be employed, depending upon the alkyl radical to be incorporated onto the benzene. If methylbenzene is to be formed, suitable alkylating agents are methanol or methyl chloride. If ethylbenzene is desired, a suitable alkylating agent can be selected from ethylene, ethanol, a monohalogenated ethane, or other species that will furnish an ethyl carbonion ion. If propylbenzene is desired, a suitable alkylating agent is propylene, isopropanol, or a halogenated propane. In a like manner, butylbenzene and pentylbenzene can be derived from similar compounds, but containing either the butyl cation or the pentyl cation.

As pointed out hereinabove, a catalyst comprising a crystalline borosilicate can be used to convert an alcohol to useful products. Suitable conditions for the conversion of alcohol to useful hydrocarbon products comprise a hot spot temperature within the range of about 650° F. (343° C.) to about 1,350° F. (732° C.), a pressure within the range of about 0.5 atm (50.7 kPa) to about 30 atm (3,040 kPa), and a WHSV within the range of about 0.1 $hr^{-1}$ to about 50 $hr^{-1}$.

Conveniently, the alcohol can be converted to hydrocarbon products boiling in the gasoline boiling range, i.e., boiling within the range of about 90° F. (32° C.) to about 400° F. (204° C.). Such products will include paraffins, naphthenes, olefins, and aromatics. The preferred products are aromatics and olefins.

Preferred conditions for the conversion of an alcohol to hydrocarbon products boiling in the gasoline boiling range comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 $hr^{-1}$ to about 8 $hr^{-1}$.

Alcohols that are suitable for use as feedstocks in the process for the conversion of an alcohol to hydrocarbon products boiling in the gasoline boiling range are alcohols containing 1 to 4 carbon atoms, such as methanol and ethanol. A preferred feed is methanol.

The AMS-1B crystalline borosilicates can also be used as adsorbents to selectively adsorb specific isomers or hydrocarbons in general from a liquid or vapor stream.

The ability for these materials to be stable under high temperatures or in the presence of other normal deactivating agents appears to make this class of crystalline materials relatively valuable for high-temperature operations including the cyclical types of fluidized catalytic cracking or other processing.

The AMS-1B crystalline borosilicates can be used as catalysts or adsorbents whether in the alkali-metal or alkaline-earth-metal forms, the ammonium form, the hydrogen form, or any other univalent or multivalent cationic form. Mixtures of cations may be employed. The AMS-1B crystalline borosilicates can also be used in intimate combination with a hydrogenating component, such as tungsten, vanadium, molybdenum, rhenium, nickel, cobalt, chromium, manganese, or a noble metal, such as platinum or palladium, or rare earth metals, where a hydrogenation-dehydrogenation function is to be performed. Such components can be exchanged into the composition at the cationic sites, represented by the term "M" in the above formulae, impregnated therein, or physically and intimately admixed therewith. In one example, platinum can be placed on the borosilicate with a platinum-metal-containing ion.

The impregnation of a hydrogenation metal on the borosilicate or on a support comprising the crystalline borosilicate suspended in and distributed throughout a matrix of a porous refractory inorganic oxide, such as an alumina, often results in a suitable catalytic composition. For example, a catalyst comprising molybdenum impregnated on a composition of AMS-1B crystalline borosilicate suspended in an alumina matrix, when used to isomerize a feed of mixed xylenes, furnishes better selectivity and higher by-product values.

The original cation associated with the AMS-1B crystalline borosilicate can be replaced, as mentioned above, by a wide variety of other cations according to techniques which are known in the art. Ion-exchange techniques known in the art are disclosed in many patents including U.S. Pat. No. 3,140,249, U.S. Pat. No. 3,140,251 and U.S. Pat. No. 3,140,253, the teachings of which are incorporated by reference into this specification.

A catalytically-active material can be placed onto the borosilicate structure by ion exchange, impregnation, or other suitable contact means, followed by washing, drying at about 150° F. (66° C.) to about 600° F. (316° C.), and then calcining in a suitable atmosphere, such as air, nitrogen, or combinations thereof, at about 500° F. (260° C.) to about 1,500° F. (816° C.), typically about 1,000° F. (538° C.), usually for about 0.5 hour to about 20 hours. This procedure can be repeated one or more times. Advantageously, before placing a catalytically-active metal ion on the borosilicate structure, the borosilicate is in the hydrogen form which, typically, is produced by exchange with ammonium ion followed by calcination.

Ion-exchange of the cationic site within the crystalline material will have a relatively insignificant effect on the overall X-ray diffraction pattern that the crystalline borosilicate material generates. Small variations may occur at various spacings on the X-ray pattern, but the overall pattern remains essentially the same. Small changes in the X-ray diffraction patterns may also be the result of processing differences during manufacture of the borosilicate; however, the material will still fall within the generic class of AMS-1B crystalline borosilicates defined in terms of their X-ray diffraction patterns as shown in the tables found herein, or in the examples that follow.

The crystalline borosilicate of the present invention may be incorporated as a pure borosilicate in a catalyst or adsorbent or may be admixed with various binders or bases depending upon the intended process use. In many instances, the crystalline borosilicate can be combined with active or inactive materials, synthetic or naturally-occurring zeolites, as well as inorganic or organic materials which would be useful for binding the borosilicate. Other well-known materials include mixtures of silica, silica-alumina, alumina sols, clays, such as bentonite or kaolin, or other binders well known in the art. The crystalline borosilicate can also be mixed intimately with porous matrix materials, such as silica-magnesia, silica-alumina, silica-thoria, or silica-titania. The crystalline borosilicate content can vary anywhere from a few up to 100 wt% of the total finished product. Typical catalytic compositions contain about 5 wt% to about 80 wt% borosilicate material.

The AMS-1B crystalline borosilicate can be prepared generally by mixing in an aqueous medium, oxides of boron, an alkali metal or an alkaline earth metal, such as sodium, and silicon, together with alkylammonium cations or a precursor of alkylammonium cations, such as an alkylamine, an alkylamine plus an alkyl alcohol, an alkylamine plus an alkyl halide, or an alkylamine plus an alkyl acetate. The alkyl groups in the alkylammonium cations may be the same, or mixed, such as tetraethyl-, or diethyl-dipropylammonium cations. The mole ratios of the various reactants can be varied considerably to produce the AMS-1B crystalline borosilicates. In particular, the mole ratios of the initial reactant concentrations for producing the borosilicate can vary as is indicated in Table VIII below.

Examples of oxides of boron are $H_3BO_3$, $B_2O_3$, and $B_4O_7$. Examples of oxides of silicon are silicic acid, sodium silicate, tetraalkyl silicates, and Ludox, which is a stabilized polymer of silicic acid manufactured by E. I. du Pont de Nemours & Co. Suitable compounds of the alkali metals or alkaline earth metals are their hydroxides.

TABLE VIII

|  | Broad | Preferred | Most Preferred |
|---|---|---|---|
| $SiO_2/B_2O_3$ | 5–400 | 10–150 | 10–80 |
| $R_2O^+/(R_2O^+ + M_{2/n}O)$ | 0.1–1 | 0.2–0.97 | 0.3–0.97 |
| $OH^-/SiO_2$ | 0.1–11 | 0.1–2 | 0.1–1 |
| $H_2O/OH^-$ | 10–4000 | 10–500 | 10–500 | where R is an alkylamine or alkylammonium cation, preferably tetra-n-propylammonium cation, tetraethyl-ammonium cation, or a cation of 1,6-diaminohexane (1,6-hexanediamine), and M is at least one cation having the valence of n, such as an alkali-metal or an alkaline-earth-metal cation. The above quantities can be varied in concentration in the aqueous medium. It is contemplated that an alkylammonium cation or a precursor of an alkylammonium cation, such as an alkylamine, can be used as a crystallization template.

During preparation, acidic conditions generally should be avoided. When alkali metal hydroxides are used, the values of the ratio of $OH^-/SiO_2$ in Table VIII should furnish a pH of the system that broadly falls within the range of about 9 to about 13.5. Advantageously, the pH of the reaction system falls within the range of about 10.5 to about 11.5. Preferably, the pH of the system is about 10.8 to about 11.2. A proper pH is conducive to the incorporation of boron into the molecular sieve structure.

By simple regulation of the quantity of boron (represented as $B_2O_3$) in the reaction mixture, it is possible to vary the $SiO_2/B_2O_3$ molar ratio in the final product in a range of from about 40 to about 600, or more. In instances where an effort is made to minimize aluminum in the borosilicate crystal structure, the molar ratios of $SiO_2/Al_2O_3$ can easily exceed a ratio of 2,000:1 to 3,000:1, or more. This ratio is generally only limited by the availability of aluminum-free raw materials.

Molar ratios of $SiO_2/B_2O_3$ in the final crystalline product can vary from 4 to about 600, or more. Actual laboratory preparations under the general conditions described herein produce $SiO_2/B_2O_3$ molar ratios starting around 60 or lower. Lower ratios might be produced using production methods which still are in the scope of the teachings of this specification. There are no established criteria for establishing at what $SiO_2/B_2O_3$ molar ratio the crystalline material ceases to be a borosilicate. It seems safe to assume that at high $SiO_2/B_2O_3$ values (above about 600), the influence of the $BO_4$ tetrahedra in the crystalline structure becomes somewhat diminished and the crystalline material no longer would be referred to as a borosilicate.

Four analytical methods have been used to study the AMS-1B crystalline borosilicate. These are: unit cell size measurements by X-ray diffraction, infrared spectroscopy, nuclear magnetic resonance spectroscopy, and ion-exchange.

Unit cell measurements of the AMS-1B crystalline borosilicates showed a linear decrease of the unit cell size with respect to an increasing boron concentration in the molecular sieve over a $SiO_2/B_2O_3$ range of about 80 to about 600. Ion-exchange in the AMS-1B borosilicate has shown also that there is one equivalent of alkali metal or alkaline earth metal per mole of boron, as required for electrovalent neutrality. Infrared spectroscopy shows changes in the pore mouth vibrational frequency where the intensity of the shoulder increases with increasing boron concentration in the molecular sieve framework. Nuclear magnetic resonance spectroscopy shows the presence of only tetrahedral boron in the AMS-1B crystalline borosilicates. Unit cell measurements and infrared spectroscopy demonstrate that the boron is incorporated in the sieve framework. Ion-exchange and nuclear magnetic resonance are consistent with this basic premise.

Under reasonably controlled conditions using the above information the claimed AMS-1B crystalline borosilicate will be produced. Typical reaction conditions include heating the reactants to a temperature of anywhere from about 77° F. (25° C.) to about 572° F. (300° C.), or higher, for a period of time of anywhere from about one hour to four weeks, or more. Preferred temperature ranges are anywhere from about 194° F. (90° C.) to about 482° F. (250° C.) with an amount of time necessary for the precipitation of the AMS-1B crystalline borosilicate. A preferred reaction time varies from about 4 hours to about 2 weeks. A more preferred temperature varies from about 212° F. (100° C.) to about 482° F. (250° C.) and a more preferred reaction time varies from about 6 hours to about 1 week. Especially preferred conditions include a temperature around 329° F. (165° C.) for a period of about 5 days.

The material thus formed can be separated and recovered by well-known means, such as filtration. This material can be mildly dried for anywhere from a few hours to a few days at varying temperatures to form a dry cake which itself can then be crushed to a powder or to small particles and extruded, pelletized, or made into forms suitable for its intended use. Typically, the material prepared after the mild drying conditions will contain the alkylammonium ion within the solid mass and a subsequent activation or calcination procedure is necessary, if it is desired to remove this material from the formed product.

Typically, the high temperature calcination conditions will take place at temperatures anywhere from about 500° F. (260° C.) to about 1,600° F. (871° C.), or higher. Extreme calcination temperatures may prove detrimental to the crystal structure or may totally destroy it. There is generally no need for going beyond about 1,100° F. (593° C.) in order to remove the alkylammonium cation from the original crystalline material formed.

In a typical preparation of an AMS-1B crystalline borosilicate, a compound of an alkali metal or an alkaline earth metal, such as sodium hydroxide, and a compound of boron, such as boric acid, are dissolved in water (preferably, distilled or deionized water). A tetraalkylammonium compound, such as tetra-n-propylammonium bromide, is added to the above solution and the pH of the resulting solution is adjusted to a value of about 11.0±0.2 by the addition of base or acid. A compound of silicon, such as polymeric silicic acid, is added rapidly to the solution, while the solution is being agitated vigorously. Vigorous agitation is continued for about 15 minutes. After the pH of the resulting solution is adjusted to about 11.0±0.2, it is placed in an autoclave that is maintained at a temperature of about 165° C. Preferably, a stirred autoclave is used. The solution is kept in the autoclave for about 5 days for crystallization. It is preferred that the crystallization temperature be maintained below the decomposition temperature of the tetraalkylammonium compound. At the completion of the crystallization, the crystalline molecular sieve is removed from the autoclave, filtered, and washed with water. The molecular sieve material is dried in a forced draft oven at 110° C. for about 16 hours and is then heated in air in a manner such that the temperature rise does not exceed 110° C. per hour until a temperature of about 1,000° F. (538° C.) is reached. Calcination at this temperature is then continued for about 4 hours.

Typically, the surface area of the resulting molecular sieve, as determined by BET surface area analysis, is about 350 m²/gm to about 390 m²/gm and the sieve particles have a maximum diameter, as determined by a scanning electron microscope, of about 2 microns.

Typically, an active hydrocarbon conversion catalyst is prepared by ion-exchanging a borosilicate, as prepared above, one or more times with an aqueous solution of ammonium acetate at a temperature of about 85° C. to 100° C. and drying, as described above, to the ion-exchanged molecular sieve. The borosilicate is converted to the hydrogen form by calcination. Then the metallic cations, for example, nickel ions, are introduced onto the borosilicate, typically, by exchanging the sieve one or more times with an aqueous solution of a compound of the metal, for example, nickelous nitrate, at a temperature of about 85° C. to about 100° C.

Then the catalyst composition is formed by dispersing the finely-divided metal-exchanged borosilicate in a sol or gel of a high-grade-purity gamma-alumina and adding, while stirring, a solution of ammonium hydroxide to promote gelation. The resulting mixture is dried and calcined, as described above, pulverized to a convenient particle size, or formed into pellets or extrudate.

Another typical powder X-ray diffraction pattern of the AMS-1B borosilicate, which pattern was obtained by means of Method No. 1 after the crystalline borosilicate had been calcined at 1,100° F. (593° C.), displays the significant lines in the indicated relative intensities (relative peak heights) and assigned strengths presented in Table IX hereinbelow:

TABLE IX

| d (Å) | Relative Intensity (I/Io) | Assigned Strength |
|---|---|---|
| 11.04 ± 0.2 | 48 | MS |
| 10.04 ± 0.2 | 34 | M |
| 6.37 ± 0.1 | 12 | W |
| 5.98 ± 0.07 | 14 | W |
| 5.68 ± 0.07 | 11 | W |
| 5.57 ± 0.05 | 14 | W |
| 4.37 ± 0.05 | 12 | W |
| 4.27 ± 0.05 | 16 | W |
| 4.07 ± 0.05 | 13 | W |
| 4.00 ± 0.05 | 10 | W |
| 3.83 ± 0.05 | 100 | VS |
| 3.72 ± 0.05 | 46 | MS |
| 3.64 ± 0.05 | 30 | M |
| 3.54 ± 0.05 | 23 | M |
| 3.42 ± 0.05 | 15 | W |
| 3.34 ± 0.05 | 12 | W |
| 3.30 ± 0.05 | 15 | W |
| 3.04 ± 0.05 | 16 | W |
| 2.98 ± 0.02 | 19 | W |
| 2.48 ± 0.02 | 13 | W |

The above X-ray pattern is characteristic of the crystalline borosilicate having the oxide mole formula described in Equation I, after the borosilicate has been calcined at 1,100° F. (593° C.) and the alkylammonium (tetraethylammonium) cation has been removed from the system by the calcination procedure.

If the crystalline borosilicate of the present invention is analyzed for an X-ray diffraction pattern when the borosilicate is in an "as-produced state" (prior to high-temperature calcination, but after some reasonable amount of drying has taken place), the X-ray diffraction pattern resulting generally is similar to that above except the relative intensities (relative peak heights) may shift locations somewhat.

Broadly, in accordance with the present invention and in view of the above, there is provided a crystalline borosilicate which comprises a molecular sieve material having the following composition in terms of mole ratios of oxides:

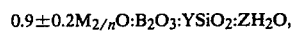

$$0.9 \pm 0.2 M_{2/n}O:B_2O_3:YSiO_2:ZH_2O,$$

wherein M is at least one cation having a valence of n, Y is within the range of about 4 to about 600, and Z is within the range of 0 to about 160.

There is provided a crystalline borosilicate which comprises a molecular sieve material providing an X-ray diffraction pattern comprising the following lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9\pm0.2M_{2/n}O:B_2O_3:YSiO_2:ZH_2O,$$

wherein M is at least one cation having a valence of n, Y is between 4 and about 600, and Z is between 0 and about 160.

The X-ray diffraction pattern suggested hereinabove in the preceding paragraph considers eight principal lines, interplanar spacings, that are characteristic of the AMS-1B crystalline borosilicates. It is to be understood that the X-ray diffraction pattern of AMS-1B crystalline borosilicates is not limited to these lines but contains other less significant lines. However, these eight principal lines are deemed sufficient to identify properly the AMS-1B crystalline borosilicate material.

Moreover, there is provided a crystalline borosilicate which comprises a molecular sieve material having the following composition in terms of mole ratios of oxides:

$$0.9\pm0.2M_{2/n}O:B_2O_3:YSiO_2:ZH_2O,$$

wherein M is at least one cation having a valence of n, Y is between 4 and about 600, and Z is between 0 and about 160, which material is prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

In addition, according to the present invention, there is provided a method for preparing a crystalline borosilicate comprising a molecular sieve material having the following composition in terms of mole ratios of oxides:

$$0.9\pm0.2M_{2/n}O: B_2O_3:YSiO_2:ZH_2O,$$

wherein M is at least one cation having a valence of n, Y is between 4 and about 600, and Z is between 0 and about 160, which method comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

Furthermore, there is provided a process for the conversion of a hydrocarbon stream, which process comprises contacting said stream at conversion conditions with a catalyst comprising a crystalline borosilicate which comprises a molecular sieve material having the following composition in terms of mole ratios of oxides:

$$0.9\pm0.2M_{2/n}O:B_2O_3:YSiO_2:ZH_2O,$$

wherein M is at least one cation having a valence of n, Y is within the range of about 4 to about 600, and Z is within the range of 0 to about 160.

There is provided a process for the conversion of a hydrocarbon stream, which process comprises contacting said stream at conversion conditions with a catalyst comprising a crystalline borosilicate which comprises a molecular sieve material having the following composition in terms of mole ratios of oxides:

$$0.9\pm0.2M_{2/n}O:B_2O_3:YSiO_2:ZH_2O,$$

wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

There is also provided a process for the catalytic isomerization of an alkylaromatic having at least two alkyl groups, which process comprises contacting said alkylaromatic at isomerization conditions with a catalyst comprising a crystalline borosilicate which comprises a molecular sieve material and providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M | and having the following composition in terms of mole ratios of oxides:

$$0.9\pm0.2M_{2/n}O:B_2O_3:YSiO_2:ZH_2O,$$

wherein M is at least one cation having a valence of n, Y is between 4 and about 600, and Z is between 0 and about 160.

In addition, there is provided a process for the catalytic isomerization of a xylene feed, which process comprises contacting said feed at isomerization conditions with a catalyst comprising a crystalline borosilicate which comprises a molecular sieve material having the following composition in terms of mole ratios of oxides:

$$0.9\pm0.2M_{2/n}O:B_2O_3:YSiO_2:ZH_2O,$$

wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

In addition, there is provided a process for the conversion of a hydrocarbon stream, which process comprises contacting said stream at conversion conditions with a catalyst comprising a crystalline borosilicate which comprises a molecular sieve material having the following composition in terms of mole ratios of oxides:

$$0.9 \pm 0.2 M_{2/n}O:B_2O_3:YSiO_2:ZH_2O,$$

wherein M is at least one cation having a valence of n, Y is between 4 and about 600, and Z is between 0 and about 160, which material is prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

There is provided a process for the catalytic isomerization of a xylene feed, which process comprises contacting said feed at isomerization conditions with a catalyst comprising a crystalline borosilicate which comprises a molecular sieve material having the following composition in terms of mole ratios of oxides:

$$0.9 \pm 0.2 M_{2/n}O:B_2O_3:YSiO_2:ZH_2O,$$

wherein M is at least one cation having a valence of n, Y is between 4 and about 600, and Z is between 0 and about 160, which material is prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

In one embodiment of the present invention, there is provided a crystalline borosilicate having a composition in terms of mole ratios of oxides as follows:

$$0.9 \pm 0.2 M_{2/n}O:B_2O_3:YSiO_2:ZH_2O,$$

wherein M is at least one cation having a valence of n, Y is between 4 and about 500, and Z is between 0 and about 160, said borosilicate showing the X-ray diffraction lines of Table V hereinabove.

In another embodiment of the present invention, there is provided a crystalline borosilicate having a composition in terms of mole ratios of oxides as follows:

$$0.9 \pm 0.2 M_{2/n}O:B_2O_3:YSiO_2:ZH_2O,$$

wherein M is at least one cation having a valence of n, Y is between 4 and about 500, and Z is between 0 and about 160, said borosilicate showing the X-ray diffraction lines and assigned strengths substantially as described in Table V hereinabove.

In another embodiment, there is provided a crystalline borosilicate having a composition in terms of mole ratios of oxides as follows:

$$0.9 \pm 0.2 M_{2/n}O:B_2O_3:YSiO_2:ZH_2O,$$

wherein M is at least one cation having a valence of n, Y is between 4 and about 300, and Z is between 0 and about 160, said borosilicate showing the X-ray diffraction lines and assigned strengths substantially as described in Table II hereinabove.

In addition, there is provided a crystalline borosilicate having a composition in terms of mole ratios of oxides as follows:

$$0.9 \pm 0.2(WR_2O + (1-W)M_{2/n}O):B_2O_3:YSiO_2:ZH_2O,$$

wherein R is tetrapropylammonium cation, M is an alkali metal cation, W is greater than 0 and less than or equal to 1, Y is between about 4 and about 500, Z is between 0 and about 160, said borosilicate showing the X-ray diffraction lines and assigned strengths substantially as described in Table VI hereinabove.

There is provided in another embodiment of the present invention a crystalline borosilicate having a composition in terms of oxides as follows:

$$0.9 \pm 0.2(WR_2O + (1-W)M_{2/n}O):B_2O_3:YSiO_2:ZH_2O,$$

wherein R is tetrapropylammonium cation, M is an alkali metal cation, W is greater than 0 and less than or equal to 1, Y is between about 4 and about 300, Z is between 0 and about 160, said borosilicate having the X-ray diffraction lines and assigned strengths substantially as described in Table IV hereinabove.

Broadly, according to the present invention, there is provided a process for conversion of a hydrocarbon, which process comprises contacting said hydrocarbon at conversion conditions with a crystalline borosilicate having a composition in terms of mole ratios of oxides as follows:

$$0.9 \pm 0.2 M_{2/n}O:B_2O_3:YSiO_2:ZH_2O,$$

wherein M is at least one cation having a valence of n, Y is in the range of from about 4 to about 500, and Z is in the range of from 0 to about 160, said borosilicate showing the X-ray diffraction lines and assigned strengths as described in Table V of the specification.

Moreover, there is provided a process for the catalytic isomerization of a xylene feed, which process comprises contacting said feed at isomerization conditions with a crystalline borosilicate having a composition in terms of mole ratios of oxides as follows:

$0.9 \pm 0.2 M_{2/n}O:B_2O_3:YSiO_2:ZH_2O$, wherein M is at least one cation having a valence of n, Y is in the range of from about 4 to about 500, and Z is in the range of from 0 to about 160, said crystalline borosilicate showing the X-ray diffraction lines and assigned strengths as described in Table V of the specification.

There is also provided a process for conversion of a hydrocarbon, which process comprises contacting said hydrocarbon at conversion conditions with a crystalline borosilicate having a composition in terms of mole ratios of oxides as follows:

$0.9 \pm 0.2 M_{2/n}O:B_2O_3:YSiO_2:ZH_2O$, wherein M is at least one cation having a valence of n, Y is in the range of from about 4 to about 300, and Z is in the range of from 0 to about 160, said crystalline borosilicate having the X-ray diffraction lines and assigned strengths substantially as described in Table II of the specification.

Furthermore, there is provided a process for the catalytic isomerization of a xylene feed, which process comprises contacting said feed at isomerization conditions with a crystalline borosilicate having a composition in terms of mole ratios of oxides as follows:

$0.9 \pm 0.2 M_{2/n}O:B_2O_3:YSiO_2:ZH_2O$, wherein M is at least one cation having a valence of n, Y is in the range of from about 4 to about 300, and Z is in the range of from 0 to about 160, said crystalline borosilicate showing the X-ray diffraction lines and assigned strengths substantially as described in Table II of the specification.

In addition, there is also provided a method for preparing a crystalline borosilicate possessing X-ray diffraction lines and relative intensities substantially as shown in Table IX hereinabove, which method comprises: (1) preparing a mixture containing an oxide of silicon, an oxide of boron, a base of an alkali or alkaline earth metal, water, and a tetraethylammonium cation, a tetra-n-butylammonium cation, or a cation of 1,6-diaminohexane (1,6-hexanediamine); and (2) maintaining said mixture at reaction conditions including a temperature in the range of from about 100° C. to about 250° C. to effect formation of said composition.

In another embodiment of the method for preparing a crystalline borosilicate having an X-ray diffraction pattern substantially as shown in Table IX, the method comprises: (1) preparing a mixture containing a tetraethylammonium cation, a tetrapropylammonium cation, or a cation of 1,6-diaminohexane (1,6-hexanediamine), an alkali or alkaline earth base, an oxide of silicon, an oxide of boron, and water and having the ratios of the initial reactant concentrations in the following ranges:

| | |
|---|---|
| $OH^-/SiO_2$ | 0.01–11 |
| $R_2O/(R_2O+M_{2/n}O)$ | 0.2–0.97 |
| $H_2O/OH^-$ | 10–4,000 |
| $SiO_2/B_2O_3$ | 5–400 | wherein R is a tetra-n-propylammonium cation, a tetraethylammonium cation, or a cation of 1,6-diaminohexane (1,6-hexanediamine), M is an alkali metal or alkaline earth metal and n is the valence of M, and (2) maintaining the reaction composition under reaction conditions including a temperature in the range of from about 100° C. to about 250° C. to effect formation of said borosilicate.

There is also provided an embodiment of the method for preparing crystalline borosilicate possessing the X-ray diffraction lines and relative intensities generally as shown in Table V, wherein the method comprises: (1) preparing a mixture containing an oxide of silicon, an oxide of boron, a base of an alkali metal or alkaline earth metal, a tetraethylammonium cation, and water; and (2) maintaining said mixture at reaction conditions including a temperature in the range of from about 100° C. to about 250° C. to effect formation of said composition.

In yet another embodiment of the method for preparing crystalline borosilicates, there is provided a method for preparing a crystalline borosilicate possessing the X-ray diffraction lines and relative intensities generally as shown in Table VI, which method comprises: (1) preparing a mixture containing an oxide of silicon, an oxide of boron, a base of an alkali metal or alkaline earth metal, a tetraethylammonium cation, a tetra-n-propylammonium cation, or a cation of 1,6-diaminohexane (1,6-hexanediamine), and water; and (2) maintaining said mixture at reaction conditions including a temperature in the range of from about 100° C. to about 250° C. to effect formation of said composition.

There is also provided a catalytic composition which comprises a crystalline borosilicate and a porous refractory inorganic oxide, said borosilicate comprising a molecular sieve material having the following composition in terms of mole ratios of oxides:

$0.9 \pm 0.2 M_{2/n}O:B_2O_3:YSiO_2:ZH_2O$, wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | said borosilicate and said inorganic oxide having been intimately admixed with one another after said borosilicate has been calcined.

In addition, there is provided a process for the conversion of a hydrocarbon stream, which process comprises contacting said stream at conversion conditions with a catalytic composition which comprises a crystalline borosilicate and a porous refractory inorganic oxide, said borosilicate comprising a molecular sieve material having the following composition in terms of mole ratios of oxides:

$0.9 \pm 0.2 M_{2/n}O:B_2O_3:YSiO_2:ZH_2O$, wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | said borosilicate and said inorganic oxide having been intimately admixed with one another after said borosilicate has been calcined.

Moreover, there is provided a process for the catalytic isomerization of a xylene feed, which process comprises contacting said feed at isomerization conditions with a catalytic composition which comprises a crystalline borosilicate and a porous refractory inorganic oxide, said borosilicate comprising a molecular sieve material having the following composition in terms of mole ratios of oxides:

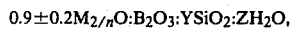

$0.9 \pm 0.2 M_{2/n}O : B_2O_3 : Y SiO_2 : Z H_2O,$ wherein M is at least one cation having a valence of n, Y is between 4 and about 600, and Z is between 0 and about 160, and providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | said borosilicate and said inorganic oxide having been intimately admixed with one another after said borosilicate has been calcined.

The following examples are presented as specific embodiments of the present invention and should not be read to unduly limit or restrict the scope of the appended claims.

EXAMPLE I

The AMS-1B crystalline borosilicate was prepared by dissolving 0.25 gm of $H_3BO_3$ and 1.6 gm of NaOH in 60 gm of distilled $H_2O$. Then 9.4 gm of tetra-n-propylammonium bromide (TPAB) were added and dissolved. Finally, 12.7 gm of Ludox AS-30 (30% solids) were added with vigorous stirring. The addition of Ludox gave a curdy, gelatinous, milky solution. This solution was placed in a crystallization vessel and sealed. The vessel was placed in a 329° F. (165° C.) oven for 7 days. At the end of this time, the vessel was opened and the contents were filtered. The recovered crystalline material was washed with copious quantities of $H_2O$ and was then dried at (329° F.) 165° C. in a forced air oven overnight. The dried material was identified by X-ray diffraction as a crystalline material having the typical AMS-1B pattern with 100% crystallinity. Its X-ray diffraction pattern is reported in Table III above. The yield was approximately 2 grams.

EXAMPLE II

In this example, the AMS-1B crystalline borosilicate of Example I was used to produce a catalyst having isomerization capabilities.

The material from Example I was calcined at 1,100° F. (593° C.) in air for 4 hours to remove the organic base. The calcined sieve was exchanged one time with a solution of 20 gm of $NH_4NO_3$ in 200 ml of $H_2O$ and then a second time with 20 gm of ammonium acetate in 200 ml of $H_2O$ at 190° F. (88° C.) for 2 hours. The exchanged borosilicate was dried and calcined in air by heating it to 900° F. (482° C.) in 4 hours, maintaining the borosilicate at 900° F. (482° C.) for 4 hours, and then cooling to 100° F. (38° C.) in 4 hours. The calcined material was exchanged with 100 ml of a 5% Ni($NO_3$)$_2 \cdot 6H_2O$ solution for 2 hours at 190° F. (88° C.). The sieve was washed with $H_2O$ and the excess Ni++ ions were washed out of the sieve. The sieve was dried and calcined again using the above procedure. About 2 gm of the borosilicate were dispersed in 16.9 gm of PHF-$Al_2O_3$ (a gamma-alumina precursor obtained from American Cyanamid Company) hydrosol (8.9% solids) and mixed thoroughly. One milliliter of distilled $H_2O$ and 1 ml of concentrated $NH_4OH$ were mixed and added to the slurry with intensive mixing. The AMS-1B/$Al_2O_3$ mix was placed in a drying oven at 329° F. (165° C.) for 4 hours. The dried material was again calcined, using the above procedure. The calcined catalyst was crushed to 30/50-mesh material, i.e., a material that would pass through a 30-mesh screen (U.S. Sieve Series) but would be retained on a 50-mesh screen (U.S. Sieve Series), and impregnated with 2 ml of a solution of 5% Ni($NO_3$)$_2 \cdot 6H_2O$ in distilled $H_2O$. The catalyst was again dried and activated by a fourth programmed calcination.

The calcined catalyst contained 65 wt% borosilicate and 35 wt% amorphous alumina with approximately 0.5 wt% of the total solid as nickel. This material was analyzed by X-ray diffraction and the results are reported in Table I above. The amorphous alumina did not significantly alter the diffraction pattern generated.

One gram of the sized and activated catalyst was placed in a microreactor and sulfided with $H_2S$ for 20 minutes at room temperature. The catalyst was then placed under $H_2$ pressure and heated to 600° F. (316° C.). After 1 hour, feed was passed through the microreactor under the following once-through conditions:

| | |
|---|---|
| Temperature | 800° F. (427° C.) |
| Pressure | 150 psig |
| WHSV | 6.28 hr$^{-1}$ |
| H/HC, mole ratio | 7 |

The liquid feed and effluent streams for this operation are shown below. Because of the equipment limitations on the screening unit, only analyses on liquid streams were obtained and reported. The lightend production over this catalyst was low from the gas chromatographic analysis made on the off-gas stream from the unit. The volume of off-gas was determined to not substantially reduce overall liquid yields over the catalyst.

| Component | Liquid Feed, wt % | Liquid Product, wt % |
|---|---|---|
| Paraffins and naphthenes | .03 | .08 |
| Benzene | — | 1.51 |
| Toluene | .077 | .26 |
| Ethylbenzene | 19.71 | 17.35 |
| para-Xylene | — | 19.43 |
| meta-Xylene | 79.80 | 46.40 |
| ortho-Xylene | .38 | 14.96 |
| C$_9$+ | — | 1.* |

*Approximate value only

EXAMPLE III

A solution of 600 gm H$_2$O, 2.5 gm H$_3$BO$_3$, and 7.5 gm of NaOH was prepared. 94.3 gm of tetra-n-propylammonium bromide was added to the original mixture and dissolved. Then 114.5 gm of Ludox AS-30 (30 wt% solids) were added to the original liquid mixture with vigorous stirring.

The resulting mixture was placed in a reaction vessel and sealed. The bomb was placed in an oven at 329° F. (165° C.) for 7 days.

After washing and drying of the recovered solids as described in Example I, an X-ray diffraction analysis of this material was performed. The crystalline borosilicate was identified as AMS-1B with an X-ray diffraction pattern as described in Table III.

EXAMPLE IV

A borosilicate similar to that prepared in Example I was calcined at about 1,100° F. (594° C.) and then analyzed to determine its overall composition. The results are shown below.

| Component | |
|---|---|
| SiO$_2$, wt % | 94.90 |
| B$_2$O$_3$ | 1.06 |
| Na$_2$O | 0.97 |
| Al$_2$O$_3$ | 0.057 |
| Fe$_2$O$_3$ | 0.029 |
| Volatiles* | 2.984 |
| Total | 100.00 |
| Mole Ratios | |
| SiO$_2$/B$_2$O$_3$ | 104.5 |
| Na$_2$O/B$_2$O$_3$ | 1.0 |
| SiO$_2$/Al$_2$O$_3$ | 2820. |
| SiO$_2$/Fe$_2$O$_3$ | 8790. |
| SiO$_2$/(Al$_2$O$_3$ + Fe$_2$O$_3$) | 2150. |

*Assumed value to total 100%.

Other borosilicates were produced as generally described in Example I, except that the H$_3$BO$_3$ content was varied resulting in SiO$_2$/B$_2$O$_3$ molar ratios varying from 50 to 160, or higher, before the borosilicate was calcined or exchanged. After exchange with suitable catalytic materials the SiO$_2$/B$_2$O$_3$ molar ratio generally increased to a value of 60–100 for an as-prepared borosilicate which had a SiO$_2$/B$_2$O$_3$ molar ratio of around 50.

EXAMPLE V

Three borosilicate materials were prepared similarly to the method described in Example I. The recovered materials were program calcined at about 1,000° F. (538° C.) and then analyzed for boron and silicon as reported below. The program calcination comprised heating from about 200° F. (93° C.) to about 1,000° F. (538° C.) in 4 hours, holding at 1,000° F. (538° C.) for 4 hours, and cooling to about 200° F. (93° C.) in 4 hours.

| Borosilicate | Wt % Boron | Molar Ratio SiO$_2$/B$_2$O$_3$ |
|---|---|---|
| A | 0.66 | 47.4 |
| B | 0.64 | 49.1 |
| C | 0.71 | 44.5 |

After ion-exchange with ammonium acetate, each borosilicate was program calcined at about 1,000° F. (538° C.) as described hereinabove. The following was then determined:

| Borosilicate | Molar Ratio SiO$_2$/B$_2$O$_3$ |
|---|---|
| A | 75.1 |
| B | 71.2 |
| C | 64.2 |

Powder X-ray diffraction analysis was performed on samples of the above borosilicates after they had been program calcined at 1,000° F. (538° C.), but prior to ion-exchange. The reported patterns are shown in Tables X, XI, and XII hereinbelow for relative intensities (I/I$_o$) of 10 or greater. Table VII hereinabove shows the interplanar spacings indicated from a strip chart for two runs of borosilicate A after a 1,000° F. (538° C.) calcination but before ion exchange.

TABLE X
(Borosilicate A)

| d (Å) | Relative Intensity (I/Io) |
|---|---|
| 11.34 | 38 |
| 10.13 | 30 |
| 6.01 | 14 |
| 4.35 | 11 |
| 4.26 | 14 |
| 3.84 | 100 |
| 3.72 | 52 |
| 3.65 | 31 |
| 3.44 | 14 |
| 3.33 | 16 |
| 3.04 | 16 |
| 2.97 | 22 |
| 2.48 | 11 |
| 1.99 | 20 |
| 1.66 | 12 |

TABLE XI
(Borosilicate B)

| d (Å) | Relative Intensity (I/Io) |
|---|---|
| 11.35 | 41 |
| 10.14 | 31 |
| 6.02 | 15 |
| 4.26 | 15 |
| 3.84 | 100 |
| 3.72 | 52 |
| 3.65 | 33 |
| 3.44 | 13 |
| 3.32 | 15 |
| 3.04 | 16 |
| 2.97 | 22 |
| 2.48 | 11 |
| 1.99 | 20 |
| 1.66 | 12 |

TABLE XII (Borosilicate C)

| d (Å) | Relative Intensity (I/Io) |
|---|---|
| 11.40 | 33 |
| 10.17 | 29 |
| 6.03 | 13 |
| 5.62 | 10 |
| 4.27 | 14 |
| 3.84 | 100 |
| 3.73 | 51 |
| 3.65 | 30 |
| 3.44 | 13 |
| 3.32 | 16 |
| 3.05 | 16 |
| 2.98 | 21 |
| 1.99 | 19 |
| 1.66 | 12 |

EXAMPLE VI

A crystalline borosilicate was prepared by dissolving 0.8 gm of $H_3BO_3$ and 4.0 gm of NaOH in 200 gm of distilled $H_2O$. Then 31.2 gm of tetraethylammonium bromide (TEAB) were added and dissolved. Finally, 29.0 gm of Ludox HS-40 (40 wt% $SiO_2$, a silica sol stabilized with sodium and produced by DuPont) were added with vigorous stirring. The addition of the Ludox silica sol gave a curdy, gelatinous, milky solution. This reaction composition was placed in a crystallization vessel, sealed, and designated reaction mixture A. The vessel was placed in a 329° F. (165° C.) oven and left there for 7 days. At the end of this time, it was opened and its contents were filtered. The recovered crystalline material was washed with copious quantities of $H_2O$ and was then dried at 329° F. (165° C.) in a forced air oven. The dried material was identified by X-ray powder diffraction analysis as a crystalline material having an X-ray diffraction pattern as reported in Table IX above. The yield was approximately 10.6 grams of solids.

Two other reaction mixtures were prepared similarly to mixture A above except that 1.6 gm (reaction mixture B) and 3.2 gm (reaction mixture C) of $H_3BO_3$, respectively, were used in the formulations. The solids recovered from mixture B amounted to 8.8 gm and from mixture C amounted to 11.3 gm. The X-ray diffraction patterns for these products were similar to the pattern as reported in Table IX above.

The mole ratios of initial reactants for reaction mixtures A, B, and C are described in the Table XIII below:

TABLE XIII

| | Mole Ratios | | |
|---|---|---|---|
| Component | Mixture A | Mixture B | Mixture C |
| $OH^-/SiO_2$ | 0.52 | 0.52 | 0.52 |
| $SiO_2/B_2O_3$ | 29.97 | 14.93 | 7.46 |
| $Na_2O/(Na_2O + R_2O)$ | 0.52 | 0.52 | 0.52 |
| $H_2O/OH$ | 120.78 | 120.78 | 120.78 |

EXAMPLE VII

Ten grams of the crystalline borosilicate produced from mixture C in Example VI were exchanged five times for 1.5 hours for each exchange at about 194° F. (90° C.) with a single solution of 15 grams ammonium acetate in 150 ml of $H_2O$. The exchanged sieve was dried at 329° F. (165° C.) and then program calcined in air for four hours at about 900° F. (482° C.), i.e., heating from about 100° F. (38° C.) to about 900° F. (482° C.) in 4 hours, holding at 900° F. (482° C.) for 4 hours, and cooling to about 100° F. (38° C.) in 4 hours.

Two grams of the above borosilicate were then impregnated with 2 grams of an aqueous solution of 5 wt% nickel nitrate. The sieve was dried with agitation and then program calcined in air for four hours at about 900° F. (482° C.) as described hereinabove.

The impregnated material was dispersed in alumina by mixing two grams of the borosilicate in 11.1 grams of PHF-alumina hydrosol (8.7 wt% solids) and stirred for one hour. Then ammonium hydroxide was added to the mixture causing it to set-up. This gel was then dried at 329° F. (165° C.) and thereafter program calcined at about 900° F. (482° C.) for four hours. The dried product was crushed and sized to 30/50-mesh particle size and then calcined again for four hours at about 900° F. (482° C.).

One gram of the 30/50-mesh borosilicate material was placed in a small screening reactor and sulfided by contacting it with $H_2S$ gas at room temperature. The sulfided catalyst was heat treated at 597° F. (314° C.) for one hour in hydrogen at 150 psig.

Then a feed was passed on a once-through operation over the catalyst at 150 psi (1,135 kPa), 797° F. (425° C.), a molar ratio of hydrogen to hydrocarbon of 6.5, and a space velocity (WHSV) of 5.9. After about 138 hours on stream the feed and liquid effluents were analyzed as shown below:

| Component | Feed, wt % | Liquid Effluent, wt % |
|---|---|---|
| Paraffins & Naphthenes | 0.05 | 0.07 |
| Benzene | — | 2.26 |
| Toluene | 0.07 | 0.56 |
| Ethylbenzene | 19.56 | 16.35 |
| para-Xylene | 8.65 | 18.63 |
| meta-Xylene | 47.83 | 41.27 |
| ortho-Xylene | 23.66 | 18.75 |
| $C_9$ + hydrocarbons | 0.22 | 2.11 |

The liquid feed and effluent analyses are shown above. Because of equipment limitations on the screening unit, only the liquid analysis is shown, the light-end production over the catalyst was low from the gas chromatographic analysis made on the off-gas stream from the unit. The volume of off-gas produced was determined to not substantially reduce the overall liquid yield. The catalyst was effective in producing paraxylene from other aromatics in the feed stream.

EXAMPLE VIII

Crystalline borosilicates produced generally as described in Example VI were identified by X-ray powder diffraction analysis. The X-ray diffraction pattern generated by this material is reproduced below for two different runs. In the second run, the reported peak intensity at 2.001 Angstroms was thought to be due in part to the alloy present in the sample holder and not totally produced by the borosilicate analyzed.

TABLE XIV

| I/Io | d (Å) | Two-Theta |
|---|---|---|
| 3 | 13.930 | 6.34 |
| 3 | 13.504 | 6.54 |
| 4 | 12.587 | 7.01 |
| 45 | 11.193 | 7.89 |

TABLE XIV-continued

| I/Io | d (Å) | Two-Theta |
|---|---|---|
| 34 | 10.041 | 8.80 |
| 3 | 9.408 | 9.39 |
| 3 | 9.154 | 9.65 |
| 3 | 8.987 | 9.83 |
| 2 | 8.732 | 10.12 |
| 3 | 8.662 | 10.20 |
| 2 | 8.534 | 10.35 |
| 2 | 8.476 | 10.42 |
| 2 | 8.319 | 10.62 |
| 2 | 8.212 | 10.76 |
| 2 | 8.126 | 10.87 |
| 2 | 7.766 | 11.38 |
| 2 | 7.689 | 11.49 |
| 3 | 7.533 | 11.73 |
| 3 | 7.400 | 11.94 |
| 3 | 7.112 | 12.43 |
| 3 | 6.992 | 12.64 |
| 7 | 6.703 | 13.19 |
| 12 | 6.367 | 13.89 |
| 16 | 5.985 | 14.78 |
| 10 | 5.696 | 15.54 |
| 13 | 5.566 | 15.90 |
| 5 | 5.380 | 16.46 |
| 4 | 5.271 | 16.80 |
| 4 | 5.119 | 17.30 |
| 10 | 4.992 | 17.74 |
| 4 | 4.867 | 18.21 |
| 3 | 4.757 | 18.63 |
| 2 | 4.712 | 18.81 |
| 8 | 4.599 | 19.28 |
| 4 | 4.486 | 19.77 |
| 12 | 4.349 | 20.40 |
| 17 | 4.252 | 20.86 |
| 12 | 4.098 | 21.66 |
| 11 | 4.002 | 22.19 |
| 100 | 3.83 | 23.15 |
| 51 | 3.712 | 23.94 |
| 32 | 3.636 | 24.45 |
| 10 | 3.466 | 25.67 |
| 13 | 3.433 | 25.92 |
| 9 | 3.370 | 26.42 |
| 13 | 3.334 | 26.70 |
| 15 | 3.304 | 26.95 |
| 8 | 3.241 | 27.49 |
| 6 | 3.157 | 28.24 |
| 7 | 3.126 | 28.52 |

TABLE XV

| I/Io | d (Å) | Two-Theta |
|---|---|---|
| 48 | 11.187 | 7.78 |
| 34 | 10.039 | 8.80 |
| 12 | 6.366 | 13.89 |
| 14 | 5.987 | 14.78 |
| 11 | 5.708 | 15.50 |
| 14 | 5.569 | 15.90 |
| 12 | 4.351 | 20.39 |
| 16 | 4.255 | 20.85 |
| 13 | 4.096 | 21.67 |
| 10 | 3.997 | 22.22 |
| 100 | 3.836 | 23.16 |
| 46 | 3.712 | 23.95 |
| 30 | 3.637 | 24.45 |
| 23 | 3.538 | 25.14 |
| 15 | 3.429 | 25.95 |
| 12 | 3.337 | 26.68 |
| 15 | 3.304 | 26.96 |
| 16 | 3.040 | 29.35 |
| 19 | 2.976 | 29.99 |
| 13 | 2.479 | 36.19 |
| 13 | 2.031 | 44.56 |
| 18 | 2.001 | 45.27 |
| 21 | 1.986 | 45.62 |
| 10 | 1.865 | 48.78 |
| 11 | 1.658 | 55.34 |

EXAMPLE IX

Borosilicate A, which was discussed in Example V hereinabove, was submitted for additional X-ray diffraction analyses. The results are presented in Tables XVI, XVII, and XVIII hereinbelow.

TABLE XVI

X-ray Diffraction Data by Method No. 1 for Borosilicate A After Calcination at 1,000° F. (538° C.)

| d (Å) | Assigned Strength | d (Å) | Assigned Strength |
|---|---|---|---|
| 11.08 | VS | 3.23 | VW |
| 9.96 | MS | 3.15 | VW |
| 7.39 | VW | 3.12 | VW |
| 6.66 | VW | 3.03 | VW |
| 6.32 | W | 2.96 | W |
| 5.95 | M | 2.84 | VW |
| 5.66 | W | 2.77 | VW |
| 5.54 | W | 2.72 | VW |
| 5.33 | VW | 2.59 | VW |
| 4.97 | VW | 2.49 | VW |
| 4.58 | VW | 2.47 | VW |
| 4.33 | VW | 2.38 | VW |
| 4.23 | W | 2.34 | VW |
| 3.98 | VW | 2.03 | VW |
| 3.82 | VS | 1.99 | VW |
| 3.70 | MS | 1.98 | VW |
| 3.62 | M | 1.94 | VW |
| 3.42 | VW | 1.90 | VW |
| 3.30 | W | 1.86 | VW |

TABLE XVII

X-ray Diffraction Data by Method No. 2 for Borosilicate A After Calcination at 1,000° F. (538° C.)

| d (Å) | Assigned Strength | d (Å) | Assigned Strength |
|---|---|---|---|
| 11.07 | MS | 3.23 | VW |
| 9.94 | MS | 3.03 | W |
| 7.38 | VW | 2.97 | W |
| 6.67 | VW | 2.84 | VW |
| 6.32 | W | 2.71 | VW |
| 5.94 | W | 2.59 | VW |
| 5.66 | VW | 2.50 | VW |
| 5.53 | W | 2.47 | VW |
| 5.33 | VW | 2.40 | VW |
| 4.97 | VW | 2.38 | VW |
| 4.58 | VW | 2.31 | VW |
| 4.33 | VW | 2.06 | VW |
| 4.23 | W | 2.00 | W |
| 3.82 | VS | 1.98 | W |
| 3.69 | MS | 1.94 | VW |
| 3.62 | M | 1.90 | VW |
| 3.42 | W | 1.86 | VW |
| 3.29 | W | | |

TABLE XVIII

X-ray Diffraction Data by Method No. 1 for Borosilicate A After Calcination at 1,100° F. (593° C.)

| d (Å) | Assigned Strength | d (Å) | Assigned Strength |
|---|---|---|---|
| 11.09 | VS | 3.30 | W |
| 9.98 | MS | 3.23 | VW |
| 7.41 | VW | 3.12 | VW |
| 6.67 | VW | 3.03 | VW |
| 6.33 | W | 2.96 | W |
| 5.96 | M | 2.85 | VW |
| 5.67 | W | 2.72 | VW |
| 5.54 | W | 2.59 | VW |
| 5.34 | VW | 2.47 | VW |
| 4.98 | VW | 2.38 | VW |
| 4.58 | VW | 2.03 | VW |
| 4.33 | VW | 2.00 | VW |

TABLE XVIII-continued

X-ray Diffraction Data by Method No. 1 for Borosilicate A After Calcination at 1,100° F. (593° C.)

| d (Å) | Assigned Strength | d (Å) | Assigned Strength |
|---|---|---|---|
| 4.24 | W | 1.98 | VW |
| 3.82 | VS | 1.94 | VW |
| 3.70 | MS | 1.90 | VW |
| 3.62 | M | 1.86 | VW |

EXAMPLE X

Powder X-ray diffraction analyses according to both Method No. 1 and Method No. 2 described hereinabove were preformed on a sample of Borosilicate B, which was discussed in Example V hereinabove. The X-ray diffraction data obtained by Method No. 1 are presented in Table XIX hereinbelow and the X-ray diffraction data obtained by Method No. 2 are presented in Table XX hereinbelow.

TABLE XIX

X-ray Diffraction Data by Method No. 1 for Borosilicate B After Calcination at 1,000° F. (538° C.)

| d (Å) | Assigned Strength | d (Å) | Assigned Strength |
|---|---|---|---|
| 11.09 | VS | 3.23 | VW |
| 9.98 | MS | 3.15 | VW |
| 7.40 | VW | 3.12 | VW |
| 6.67 | VW | 3.03 | W |
| 6.33 | W | 2.97 | W |
| 5.96 | M | 2.93 | VW |
| 5.67 | W | 2.85 | VW |
| 5.54 | W | 2.77 | VW |
| 5.34 | VW | 2.72 | VW |
| 5.10 | VW | 2.59 | VW |
| 4.98 | VW | 2.50 | VW |
| 4.59 | VW | 2.47 | VW |
| 4.34 | VW | 2.40 | VW |
| 4.24 | W | 2.38 | VW |
| 4.05 | VW | 2.34 | VW |
| 3.98 | VW | 2.03 | VW |
| 3.83 | VS | 2.00 | VW |
| 3.70 | MS | 2.00 | VW |
| 3.63 | M | 1.98 | VW |
| 3.46 | VW | 1.94 | VW |
| 3.42 | VW | 1.90 | VW |
| 3.32 | VW | 1.86 | VW |
| 3.29 | W | | |

TABLE XX

X-ray Diffraction Data by Method No. 2 for Borosilicate B After Calcination at 1,000° F. (538° C.)

| d (Å) | Assigned Strength | d (Å) | Assigned Strength |
|---|---|---|---|
| 11.09 | MS | 3.16 | VW |
| 9.97 | M | 3.12 | VW |
| 7.39 | VW | 3.03 | W |
| 6.67 | VW | 2.97 | W |
| 6.33 | W | 2.93 | VW |
| 5.96 | W | 2.85 | VW |
| 5.68 | W | 2.77 | VW |
| 5.55 | W | 2.72 | VW |
| 5.33 | VW | 2.67 | VW |
| 5.10 | VW | 2.64 | VW |
| 4.98 | VW | 2.59 | VW |
| 4.59 | VW | 2.50 | VW |
| 4.34 | VW | 2.47 | VW |
| 4.24 | W | 2.40 | VW |
| 4.06 | VW | 2.38 | VW |
| 3.98 | VW | 2.31 | VW |
| 3.83 | VS | 2.10 | VW |
| 3.70 | MS | 2.06 | VW |

TABLE XX-continued

X-ray Diffraction Data by Method No. 2 for Borosilicate B After Calcination at 1,000° F. (538° C.)

| d (Å) | Assigned Strength | d (Å) | Assigned Strength |
|---|---|---|---|
| 3.63 | M | 2.00 | W |
| 3.46 | VW | 1.98 | W |
| 3.42 | W | 1.94 | VW |
| 3.33 | W | 1.90 | VW |
| 3.29 | W | 1.86 | VW |
| 3.23 | VW | | |

EXAMPLE XI

Another AMS-1B crystalline borosilicate, hereinafter identified as Borosilicate D, was prepared.

Powder X-ray diffraction analyses according to both Method No. 1 and Method No. 2 described hereinabove were performed on a sample of Borosilicate D. The X-ray diffraction data obtained by Method No. 1 are presented in Table XXI hereinbelow and the X-ray diffraction data obtained by Method No. 2 are presented in Table XXII hereinbelow.

TABLE XXI

X-ray Diffraction Data by Method No. 1 for Borosilicate D After Calcination at 1,000° F. (538° C.)

| d (Å) | Assigned Strength | d (Å) | Assigned Strength |
|---|---|---|---|
| 11.09 | VS | 3.29 | W |
| 9.95 | MS | 3.23 | VW |
| 7.41 | VW | 3.15 | VW |
| 6.66 | VW | 3.12 | VW |
| 6.32 | W | 3.03 | W |
| 5.95 | M | 2.96 | W |
| 5.67 | W | 2.85 | VW |
| 5.54 | W | 2.76 | VW |
| 5.34 | VW | 2.71 | VW |
| 4.98 | VW | 2.59 | VW |
| 4.58 | VW | 2.47 | VW |
| 4.33 | VW | 2.38 | VW |
| 4.23 | W | 2.00 | VW |
| 3.82 | VS | 1.98 | VW |
| 3.70 | MS | 1.94 | VW |
| 3.62 | M | 1.90 | VW |
| 3.42 | VW | 1.86 | VW |

TABLE XXII

X-ray Diffraction Data by Method No. 2 for Borosilicate D After Calcination at 1,000° F. (538° C.)

| d (Å) | Assigned Strength | d (Å) | Assigned Strength |
|---|---|---|---|
| 11.15 | MS | 3.43 | VW |
| 10.01 | M | 3.30 | W |
| 7.42 | VW | 3.24 | VW |
| 6.70 | VW | 3.04 | W |
| 6.35 | VW | 2.97 | W |
| 5.98 | W | 2.72 | VW |
| 5.68 | VW | 2.50 | VW |
| 5.56 | W | 2.48 | VW |
| 5.35 | VW | 2.39 | VW |
| 4.99 | VW | 2.32 | VW |
| 4.60 | VW | 2.07 | VW |
| 4.35 | VW | 2.00 | W |
| 4.25 | W | 1.99 | W |
| 3.84 | VS | 1.94 | VW |
| 3.71 | MS | 1.91 | VW |
| 3.63 | M | 1.86 | VW |

EXAMPLE XII

Some of the characteristic X-ray diffraction interplanar spacings and their corresponding assigned strengths for the borosilicates presented hereinabove are compiled in Table XXIII hereinbelow. "Method" indicates the method of X-ray analysis employed, while "Treat" represents the temperature at which the particular material was calcined.

TABLE XXIII

BOROSILICATE

| TABLE | I | | III | | V | | VI | | VII | | IX | | X | | XI | | XII | |
|---|---|---|---|---|---|---|---|---|---|---|---|---|---|---|---|---|---|---|
| METHOD | 1 | | 1 | | 2 | | 2 | | 2 | | 1 | | 2 | | 2 | | 2 | |
| TREAT | 1,100° F. d (Å) | (593° C.) A.S.* | 329° F. d (Å) | (165° C.) A.S. | 1,000° F. d (Å) | (538° C.) A.S. | 329° F. d (Å) | (165° C.) A.S. | 1,000° F. d (Å) | (538° C.) A.S. | 1,100° F. d (Å) | (593° C.) A.S. | 1,000° F. d (Å) | (538° C.) A.S. | 1,000° F. d (Å) | (538° C.) A.S. | 1,000° F. d (Å) | (538° C.) A.S. |
| | 11.04 | VS | 11.04 | S | 11.3 | M | 11.4 | W | 11.3 | M | 11.04 | MS | 11.34 | M | 11.35 | MS | 11.40 | M |
| | 10.04 | MS | 9.82 | S | 10.1 | M | 10.1 | W | 10.2 | M | 10.04 | M | 10.13 | M | 10.14 | M | 10.17 | M |
| | 5.98 | M | 5.90 | W | 6.01 | W | | | 5.98 | W | 5.98 | W | 6.01 | W | 6.02 | W | 6.03 | W |
| | 3.83 | VS | 3.80 | VS | 3.84 | VS | 3.84 | VS | 3.85 | VS | 3.83 | VS | 3.84 | VS | 3.84 | VS | 3.84 | VS |
| | 3.72 | MS | 3.67 | S | 3.72 | MS | 3.73 | MS | 3.72 | MS | 3.72 | MS | 3.72 | MS | 3.72 | MS | 3.73 | MS |
| | 3.64 | M | 3.60 | MS | 3.65 | M | 3.66 | M | 3.64 | M | 3.64 | M | 3.65 | M | 3.65 | M | 3.65 | M |
| | 2.98 | W | 2.96 | W | 2.97 | M | 2.98 | W | 2.96 | M | 2.98 | W | 2.97 | M | 2.97 | M | 2.98 | M |
| | 1.99 | W | 1.99 | W | 1.99 | M | 1.99 | W | 1.99 | | 1.99 | M | 1.99 | M | 1.99 | M | 1.99 | W |

BOROSILICATE

| TABLE | XIV | | XV | | XVI | | XVII | | XIX | | XX | | XXI | | XXII | | XVIII | |
|---|---|---|---|---|---|---|---|---|---|---|---|---|---|---|---|---|---|---|
| METHOD | 1 | | 1 | | A 2 | | A 2 | | B 1 | | B 2 | | D 1 | | D 2 | | A 1 | |
| TREAT | 329° F. d (Å) | (165° C.) A.S. | 329° F. d (Å) | (165° C.) A.S. | 1,000° F. d (Å) | (538° C.) A.S. | 1,000° F. d (Å) | (538° C.) A.S. | 1,000° F. d (Å) | (538° C.) A.S. | 1,000° F. d (Å) | (538° C.) A.S. | 1,000° F. d (Å) | (538° C.) A.S. | 1,000° F. d (Å) | (538° C.) A.S. | 1,000° F. d (Å) | (538° C.) A.S. |
| | 11.19 | MS | 11.19 | MS | 11.08 | VS | 11.07 | MS | 11.09 | VS | 11.09 | MS | 11.09 | VS | 11.15 | MS | 11.09 | VS |
| | 10.04 | M | 10.04 | M | 9.96 | MS | 9.94 | MS | 9.98 | MS | 9.97 | M | 9.95 | MS | 10.01 | M | 9.98 | MS |
| | 5.99 | W | 5.99 | W | 5.95 | M | 5.94 | W | 5.96 | M | 5.96 | W | 5.95 | M | 5.98 | W | 5.96 | M |
| | 3.84 | VS | 3.84 | VS | 3.82 | VS | 3.82 | VS | 3.83 | VS | 3.83 | VS | 3.82 | VS | 3.84 | VS | 3.82 | VS |
| | 3.71 | MS | 3.71 | MS | 3.70 | MS | 3.69 | MS | 3.70 | MS | 3.70 | MS | 3.70 | MS | 3.71 | MS | 3.70 | MS |
| | 3.64 | M | 3.64 | M | 3.62 | M | 3.62 | M | 3.63 | M | 3.63 | M | 3.62 | M | 3.63 | M | 3.62 | M |
| | | | 2.98 | M | 2.96 | W | 2.97 | W | 2.97 | W | 2.97 | W | 2.96 | W | 2.97 | W | 2.96 | W |
| | | | 1.99 | | 1.99 | VW | 1.98— 2.00 | | 1.98— 2.00 | VW | 1.98— 2.00 | | 1.98— 2.00 | VW | 1.99— 2.00 | | 1.99— 2.00 | VW |

*A.S. = assigned strength

The data in Table XXIII are summarized in Table XXIV in ranges of values.

TABLE XXIV

| | X-ray Diffraction Data Summary | | |
|---|---|---|---|
| | Assigned Strengths After Treatment | | |
| d (Å) | at 538° C. | at 593° C. | at 165° C. |
| 11.04–11.40 | M-MS | MS-VS | W-MS |
| 9.82–10.20 | M-MS | M-MS | W-MS |
| 5.90–6.03 | W-M | W-M | W |
| 3.80–3.85 | VS | VS | VS |
| 3.67–3.73 | MS | MS | MS |
| 3.60–3.65 | M | M | M-MS |
| 2.96–2.98 | W-M | W | W |
| 1.98–2.00 | VW-M | W-M | W-M |

In view of the values presented in Table XXIV, the X-ray diffraction patterns of crystalline AMS-1B borosilicates can be represented in general terms by the information shown in Table XXV hereinbelow.

TABLE XXV

| | X-ray Diffraction Patterns of AMS-1B Borosilicates | |
|---|---|---|
| | Assigned Strengths For | |
| d (Å) | All | Calcined at 538° C.–593° C. |
| 11.2 ± 0.2 | W-VS | M-VS |
| 10.0 ± 0.2 | W-MS | M-MS |
| 5.97 ± 0.07 | W-M | W-M |
| 3.82 ± 0.05 | VS | VS |
| 3.70 ± 0.05 | MS | MS |
| 3.62 ± 0.05 | M-MS | M |
| 2.97 ± 0.02 | W-M | W-M |
| 1.99 ± 0.02 | VW-M | VW-M |

Therefore, in broad terms, the X-ray diffraction patterns of crystalline AMS-1B borosilicates comprise the interplanar spacings shown in Table XXV and the assigned strengths shown therein depending upon the presence or absence of calcination of the material prior to X-ray diffraction analysis.

EXAMPLE XIII

As mentioned hereinabove, the alkylammonium cations can be furnished by various compounds. To demonstrate this, 5 borosilicates were prepared by employing tetraethylammonium bromide, tetrabutylammonium bromide, or 1,6-hexanediamine as the source or precursor of the alkylammonium cations. Reactants were used in the amounts listed in Table XXVI hereinbelow. The mixtures of reactants were crystallized at 329° F. (165° C.) for 7 days. The resulting solid material was removed by filtration and washed with distilled water. The solid material was dried at 329° F. (165° C.) and then program calcined at about 1,000° F. (538° C.) for 4 hours as described hereinabove. In all 5 of these preparations, the solid materials were identified by X-ray diffraction as AMS-1B borosilicates.

TABLE XXVI

| | Preparation Information | | | | |
|---|---|---|---|---|---|
| Borosilicate | E | F | G | H | I |
| H$_2$O, gm | 200 | 200 | 200 | 600 | 600 |
| NaOH, gm | 4.0 | 4.0 | 4.0 | 5.0 | 6.0 |
| H$_3$BO$_3$, gm | 0.8 | 1.6 | 3.2 | 5.0 | 10.0 |
| Precursor* Type | TEAB | TEAB | TEAB | TBAB | 1,6-DH |
| wt., gm | 31.2 | 31.2 | 31.2 | 100.0 | 100.0 |
| Ludox Type | HS-40 | HS-40 | HS-40 | HS-40 | HS-40 |
| wt., gm | 29.0 | 29.0 | 29.0 | 76.0 | 77.5 |

TABLE XXVI-continued

| | Preparation Information | | | | |
|---|---|---|---|---|---|
| Borosilicate | E | F | G | H | I |
| Boron, wt % | — | — | — | 0.39 | 0.62 |

*Precursor of alkylammonium cations
TEAB  tetraethylammonium bromide
TBAB  tetrabutylammonium bromide
1,6-DH  1,6-diaminohexane

EXAMPLE XIV

Another catalyst was prepared. This catalyst was employed subsequently for the alkylation of benzene with ethylene to produce ethylbenzene.

A sample of crystalline AMS-1B borosilicate material was prepared first. The following components were dissolved, in the order shown, in 11.815 kg of distilled water at room temperature in a 5-gallon stirred Autoclave pressure reactor: 590 gm of boric acid (H$_3$BO$_3$), 330 gm of sodium hydroxide, and 1,945 gm of tetrapropylammonium bromide (TPAB). To the resulting solution were added 1,965 gm of Ludox HS-40. The pH of the resulting mixture was found to be 10.70.

The reactor was sealed, heated to a temperature of 329° F. (165° C.) under an autogenous pressure of 100 psi (790 kPa) to 115 psi (894 kPa), while the contents of the reactor were stirred at a rate of 250 rpm. The reaction was conducted under these conditions for three days. The heating was then discontinued and the reactor was allowed to cool overnight (approximately 16 hours). The contents were drained from the reaction vessel and were filtered through a No. 1 Whatman qualitative filter paper. The filter cake was washed with 10 liters of distilled water and dried in air for 40 hours at a temperature of 230° F. (110° C.).

A portion of the dried cake was program calcined subsequently at a temperature of 1,000° F. (538° C.) by heating the dried material at a rate of 200° F./hour (110° C./hour) and holding the material at 1,000° F. (538° C.) for 12 hours. The calcined material was shown by X-ray diffraction analysis to be 100% AMS-1B crystalline borosilicate. The molar ratio of silica to boria (SiO$_2$/B$_2$O$_3$) was shown by chemical analysis to be 49.7:1.

A portion of the calcined crystalline borosilicate material was ion-exchanged at a temperature of 90° F. (32° C.) for 1.5 hours with a 10% solution of ammonium acetate in distilled water (ratio of borosilicate:ammonium acetate was 1:1). Five separate exchanges were performed. Between exchanges, the slurry was vacuum filtered and was washed twice with distilled water, each wash being conducted with a volume of water in ml equal to three times the weight of borosilicate in gm. The cation-exchanged crystalline borosilicate was dried in a vacuum oven at a temperature of 176° F. (80° C.) for two hours and calcined as before to yield the hydrogen form of AMS-1B crystalline borosilicate.

The resulting hydrogen-form borosilicate material was wetted with distilled water in a blender in a ratio of 1:2 and mixed subsequently with a hydrosol of gamma-type alumina obtained from the American Cyanamid Company. Sufficient alumina hydrosol was employed to provide a ratio of borosilicate:alumina of 15:85. The mixture was blended for a period of five minutes. Then an ammonium hydroxide solution, prepared by diluting concentrated ammonium hydroxide with distilled water in a ratio of 1:1, was added to provide a ratio of 0.9 ml of concentrated ammonium hydroxide per gm of dry alumina. The resulting gel was blended for an additional one minute and dried at a temperature of 257° F. (125° C.) for a period of about 16 hours. The dried gel was then passed through screens to provide 18/30-mesh granular material, that is, a granular material that will pass through an 18-mesh screen (U.S. Sieve Series), but will be retained on a 30-mesh screen (U.S. Sieve Series). The screened material was then calcined in air at a temperature of 1,000° F. (538° C.) for 12 hours. The calcined material had a silica-to-boria molar ratio of 69.3:1 and was the catalyst that was used in the following benzene alkylation test.

For the following alkylation test involving the alkylation of benzene with ethylene, a single reactor was used to simulate four stages of a multi-stage reactor. This was accomplished by recycling as feed to the next stage the collected condensed product and the simulated non-condensibles from the preceding stage together with a fresh supply of ethylene and make-up benzene. A fresh catalyst charge was used for each simulated stage and the size of the charge increased to maintain approximately the same overall contact time in each stage.

To simulate the use of a dilute ethylene feed source, such as from a refinery fluid cracking unit (FCU), pure ethylene was diluted with nitrogen to approximately 15 vol % ethylene and the inerts level was allowed to build up with each succeeding stage. The total ethylene feed was divided equally among the four simulated stages and additional benzene was added to maintain a molar ratio of benzene:ethylene of 20:1 in the feed stream to each simulated stage.

The following conditions were employed for this alkylation test: a pressure of 250 psig (1,824 kPa), an inlet temperature of 800° F. (427° C.)±5° F. (2.8° C.), an ethylene feed concentration of 15±1 vol %, and a total liquid hydrocarbon WHSV based upon the total weight of the catalyst varying between 45 $hr^{-1}$ in the first stage to 30 $hr^{-1}$ in the fourth stage. The WHSV of ethylene fell within the range of 0.8 $hr^{-1}$ to 0.4 $hr^{-1}$. The ratio of benzene:ethylene was 20:1.

The results of this alkylation test are presented hereinbelow in Table XXVII.

TABLE XXVII

| Data from Alkylation-of-Benzene Test | | | | |
|---|---|---|---|---|
| Reaction Stage | 1 | 2 | 3 | 4 |
| Liquid Hydrocarbon WHSV, $hr^{-1}$ | 45 | 38 | 34 | 30 |
| Ethylene WHSV, $hr^{-1}$ | 0.8 | 0.6 | 0.6 | 0.4 |
| Average Reaction Temp., °F. | 827 | 817 | 823 | 822 |
| °C. | 442 | 436 | 440 | 439 |
| Relative Catalyst Charge | 1 | 1.25 | 1.5 | 1.8 |
| Run Length, Days | 20 | 8 | 15 | 6 |
| Ethylene Conversion, % | 99+ | 97+ | 96+ | 94+ |
| Avg. Ethylene Molar Selectivities To: | | | | |
| Ethylbenzene + Diethylbenzene | 99.4 | 99.3 | 98.9 | 98.3 |
| Toluene and Lights | 0.09 | 0.19 | 0.19 | 0.75 |
| Xylenes | 0.05 | 0.07 | 0.12 | 0.18 |
| $C_9$—Aromatics | 0.19 | 0.25 | 0.48 | 0.60 |
| Styrene | 0.05 | 0.13 | 0.24 | 0.18 |
| $C_{10}$—Aromatics | 0.05 | 0.06 | 0.07 | 0.06 |

As shown in Table XXVII, 99+% ethylene conversion was achieved in the first simulated stage and the average molar ethylene selectivity to ethylbenzene plus diethylbenzenes was 99.4%. In the fourth simulated stage, where ethylene partial pressure was lower due to the buildup of inerts, the average conversion was about 94% and selectivity was 98+%.

As shown hereinabove, there is provided a process for the alkylation of an aromatic hydrocarbon, which process comprises contacting a feed comprising said hydrocarbon under alkylation conditions and in the presence of an alkylating agent with a catalyst comprising a crystalline borosilicate which comprises a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9\pm0.2\ M_{2/n}O:B_2O_3:YSiO_2:ZH_2O,$$

wherein M is at least one cation having a valence of n, Y is between 4 and about 600, and Z is between 0 and about 160.

Furthermore, another embodiment of the present invention provides a process for the alkylation of benzene, which process comprises contacting said benzene under alkylation conditions and in the presence of an alkylating agent with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9\pm0.2\ M_{2/n}O:B_2O_3:YSiO_2:ZH_2O,$$

wherein M is at least one cation having a valence of n, Y is within the range of about 4 to about 600, and Z is within the range of 0 to about 160.

In yet another embodiment, there is provided a process for the alkylation of benzene, which process comprises contacting a feed comprising said benzene with a catalyst under alkylation conditions and in the presence of an alkylating agent, said catalyst comprising a crystalline borosilicate and a porous refractory inorganic oxide, said borosilicate and said inorganic oxide having been intimately admixed with one another, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2\, M_{2/n}O:B_2O_3:YSiO_2:ZH_2O,$$

wherein M is at least one cation having a valence of n, Y is within the range of about 4 to about 600, and Z is within the range of 0 to about 160.

Alkylation conditions are discussed hereinabove. The use of cation-exchanged AMS-1B crystalline borosilicates in a matrix material, such as a catalytically active alumina, provides a preferred catalytic composition for the alkylation of benzene. The crystalline borosilicate can be cation-exchanged suitably with a hydrogen-ion precursor. Particularly preferred is the use of ethylene as an alkylating agent to produce ethylbenzene.

EXAMPLE XV

In this example, methanol was converted in the presence of a catalytic composition comprising AMS-1B crystalline borosilicate.

Another sample of AMS-1B borosilicate material was prepared by using the following quantities of chemicals:

| | |
|---|---|
| Distilled Water, gm | 11,000 |
| NaOH, gm | 380 |
| H$_3$BO$_3$, gm | 550 |
| TPAB, gm | 850 |
| Ludox HS-40 | 3,375 |

The initial crystallization solution was made in five distinct batches, where exactly 1/5 of each of the chemical reagents was used for each batch. The NaOH and the H$_3$BO$_3$ were dissolved in distilled water. To this solution was added the TPAB. Then the Ludox HS-40 was added. The resulting slurry was then blended at a low speed of about 500 rpm with a Super-Dispax mixer. The other 4 batches of crystallization slurry were then prepared exactly as described hereinabove. Each of the five slurry preparations was charged to a 5-gallon Autoclave and the combined material was thoroughly blended. The pH of the final crystallization solution was 10.79.

The slurry was then crystallized at a temperature of 293° F. (145° C.) for six days. During this crystallization, the stirrer speed of the Autoclave reactor was approximately 500 rpm.

The product was removed from the Autoclave and was filtered. The crystallization solution had a final pH of 11.26. The filler cake was washed with a total of 20 liters of distilled water, dried on a filter, and then dried at a temperature of 329° F. (165° C.) for 24 hours. The dried solid material was then program calcined at a temperature of 1,000° F. (538° C.) by heating the material at a rate of 200° F./hour (110° C./hour) from an initial temperature of 199° F. (93° C.) to a temperature of 1,000° F. (538° C.) and holding the material at 1,000° F. (538° C.) for 12 hours. Then the calcined material was allowed to cool at a maximum rate of 110° C./hour to room temperature.

A sample of the calcined material was identified as AMS-1B crystalline borosilicate by X-ray diffraction analysis. A total of 1,436 gm of AMS-1B crystalline borosilicate was obtained from this preparation.

The resulting AMS-1B crystalline borosilicate material was converted subsequently to the ammonium form by cation-exchanging the material with ammonium acetate solution. Five exchange steps were employed. For each exchange step, 100 grams of the AMS-1B borosilicate were contacted with 1 liter of distilled water which contained 100 grams of ammonium acetate. In each case, the contact was for a period of 1.5 hours at a temperature of about 203° F. (95° C.). Of course, the same 100 grams of borosilicate material were used for each exchange. Following the first four exchange steps, the solid material was washed with 200 ml of distilled water. After the fifth exchange step, the solid material was washed with 500 ml of distilled water.

The exchanged AMS-1B crystalline borosilicate material was then dried at a temperature of 230° F. (110° C.) overnight (approximately 16 hours) and was program calcined as described in this example hereinabove. However, in this case, the material was held at the temperature of 1,000° F. (538° C.) for a period of only four hours.

The calcined material represented the hydrogen form of AMS-1B crystalline borosilicate material.

The crystalline borosilicate material in the hydrogen form was then cation-exchanged with a nickelous nitrate [Ni(NO$_3$)$_2$.6H$_2$O] solution at a temperature of 190° F. (93° C.) for a period of 1.5 hours. The nickelous nitrate solution had been prepared by dissolving 75 gm of nickelous nitrate in 1,500 ml of distilled water.

The nickel-exchanged molecular sieve material was then filtered from the exchange solution and washed with 300 ml of distilled water, dried in air at a temperature of 230° F. (110° C.) overnight (approximately 16 hours), and program calcined as described hereinabove, with the exception that the material was held at a temperature of 1,000° F. (538° C.) for a period of only four hours.

After adding 100 milliliters of distilled water to fill the sieve particle cavities, the wet AMS-1B crystalline borosilicate material was blended into 619 gm of PHF-alumina hydrosol obtained from the American Cyanamid Company. A Waring Blendor was employed for this blending. The blended alumina hydrosol-borosilicate mixture was gelled by adding a solution prepared by adding 30 ml of concentrated ammonium hydroxide to 30 ml of distilled water. The resulting gel was dried in air at a temperature of 230° F. (110° C.) overnight (approximately 16 hours) and subsequently program calcined as described hereinabove with the solid material being held at a temperature of 1,000° F. (538° C.) for a period of only four hours.

The calcined material was crushed and sieved to obtain a 30/50-mesh material, that is, a material that will pass through a 30-mesh screen (U.S. Sieve Series), but be retained on a 50-mesh screen (U.S. Sieve Series). The sized catalytic material was recalcined with the procedure that was described hereinabove. This calcined material was made up of 65 wt% AMS-1B crystalline borosilicate in the nickel and hydrogen form and 35 wt% gamma-alumina. A 20-gm (45-ml) portion of the sieved catalyst was diluted linearly with 107 gm (54 ml) of alpha-alumina and charged to a plug-flow reactor.

Reagent-grade methanol, obtained from Fisher Scientific Co., was pumped to the reactor at a pressure that was only slightly greater than the 1-psig pressure used to force part of the product gas stream to an on-line gas chromatograph analyzer. The results of the test are presented hereinbelow in Table XXVIII. The variables of temperature and weight hourly space velocity (WHSV) were changed for each cut, as shown in Table XXVIII. The cut numbers represent the order in which the various cuts were made.

The product yield data that are presented in Table XXVIII represent a careful blending of data obtained on the total gas sample and on a total liquid sample.

TABLE XXVIII

Data from Methanol-Conversion Test

| Cut No. | 1A | 1B | 1C | 5B | 5C | 6A | 6B | 2A | 2B |
|---|---|---|---|---|---|---|---|---|---|
| Hot Spot Temperature[D], °F. | 840 | 920 | 960 | 680 | 720 | 760 | 800 | 880 | 920 |
| °C. | 449 | 493 | 516 | 360 | 382 | 404 | 427 | 471 | 493 |
| WHSV, hr$^{-1}$ | 5.92 | 5.96 | 6.30 | 3.05 | 2.98 | 3.10 | 2.95 | 3.04 | 3.03 |
| Hydrocarbon Fraction in Gas | 0.7722 | 0.7186 | 0.7773 | 0.5275 | 0.5425 | 0.5212 | 0.5317 | 0.7636 | 0.7949 |
| Product Yield, % | | | | | | | | | |
| Methane | 6.6 | 8.0 | 5.4 | 0.6 | 0.8 | 0.9 | B | 9.8 | 10.6 |
| Ethane and Ethylene | 7.0 | 7.3 | 6.7 | 4.4 | 4.3 | 3.9 | B | 10.6 | 14.2 |
| Propane | 2.1 | 2.4 | 2.4 | 1.7 | 2.3 | — | B | 4.3 | 3.7 |
| Propylene | 22.8 | 20.4 | 22.6 | 11.2 | 9.9 | 11.7 | B | 23.9 | 28.3 |
| n-Butane | — | — | — | — | — | — | — | — | — |
| Isobutane | 4.0 | 3.9 | 4.4 | 5.7 | 7.4 | 7.1 | B | 4.8 | 2.6 |
| 1-Butene | 1.0 | 1.2 | 1.3 | 0.9 | 1.2 | 1.3 | B | 1.9 | 1.3 |
| Isobutylene | 13.7 | 11.9 | 14.7 | 9.1 | 8.7 | 8.1 | B | 10.8 | 10.3 |
| trans-2-Butene | 5.7 | 5.0 | 6.0 | 3.7 | 3.4 | 3.3 | B | 4.5 | 4.3 |
| cis-2-Butene | 4.2 | 3.7 | 4.4 | 2.5 | 2.3 | 2.1 | B | 3.3 | 3.2 |
| C$_5$ + P&N's and Benzene | 18.7 | 19.5 | 20.2 | 50.2 | 50.4 | 50.9 | (35.4)[B] | 3.9 | 0.9 |
| Toluene | 2.1 | 2.8 | 2.1 | 3.4 | 2.7 | 3.0 | 3.1 | 4.2 | 4.8 |
| Ethylbenzene | 0.2 | 0.3 | 0.2 | — | — | — | — | 0.4 | 0.4 |
| p-Xylene | 1.5 | 1.8 | 1.5 | 1.3 | 1.0 | 1.2 | 1.5 | 2.5 | 2.1 |
| m-Xylene | 2.7 | 3.3 | 2.7 | 2.2 | 2.3 | 2.6 | 2.9 | 5.8 | 4.7 |
| o-Xylene | 0.9 | 1.1 | 0.9 | 0.2 | 0.2 | 0.2 | 0.5 | 1.9 | 1.6 |
| Methylethylbenzene | 0.9 | 1.2 | 0.9 | — | 0.1 | 0.9 | 0.6 | 0.8 | 0.6 |
| Trimethylbenzene | 4.6 | 5.3 | 3.9 | 3.0 | 2.8 | 2.6 | 2.8 | 6.4 | 5.2 |
| Tetramethylbenzene[A] | 0.6 | 0.8 | 0.7 | — | — | — | — | — | — |
| Time on Stream, hrs.[C] | 3.75 | 4.75 | 5.75 | 30.59 | 33.03 | 37.09 | 40.01 | 8.75 | 10.75 |

| Cut No. | 2C | 4A | 7A | 4B | 5A | 3A | 3B | 3C |
|---|---|---|---|---|---|---|---|---|
| Hot Spot Temperature[D], °F. | 960 | 680 | 720 | 760 | 800 | 840 | 880 | 920 |
| °C. | 516 | 360 | 382 | 404 | 427 | 449 | 471 | 493 |
| WHSV, hr$^{-1}$ | 3.13 | 1.58 | 1.58 | 1.58 | 1.60 | 1.54 | 1.52 | 1.50 |
| Hydrocarbon Fraction in Gas | 0.8251 | 0.4600 | 0.4110 | 0.4625 | 0.5564 | 0.6800 | 0.7256 | 0.7904 |
| Product Yield, % | | | | | | | | |
| Methane | 10.5 | 0.7 | 0.7 | 0.9 | 1.4 | 3.3 | 4.8 | 7.4 |
| Ethane and Ethylene | 15.9 | 4.8 | 3.6 | 3.7 | 4.3 | 8.1 | 11.6 | 15.3 |
| Propane | 3.1 | 2.2 | 2.4 | 2.9 | 4.1 | 6.4 | 6.8 | 5.8 |
| Propylene | 31.4 | 7.8 | 5.9 | 7.3 | 11.3 | 18.3 | 23.3 | 28.1 |
| n-Butane | — | — | — | — | — | 3.0 | 2.7 | 1.9 |
| Isobutane | 1.9 | 8.7 | 7.9 | 9.7 | 8.6 | 9.2 | 7.3 | 4.5 |
| 1-Butene | 1.0 | 1.1 | 1.2 | 1.6 | 2.2 | 1.0 | 1.2 | 1.5 |
| Isobutylene | 10.5 | 6.2 | 5.0 | 6.1 | 7.2 | 8.1 | 8.7 | 8.4 |
| trans-2-Butene | 4.3 | 2.4 | 2.0 | 2.3 | 2.9 | 3.8 | 3.6 | 3.7 |
| cis-2-Butene | 3.2 | 1.6 | 1.3 | 1.5 | 2.0 | 2.6 | 2.4 | 2.4 |
| C$_5$ + P&N's and Benzene | 0.6 | 44.3 | 55.0 | 38.8 | 38.5 | 8.6 | 12.1 | 0.0 |
| Toluene | 3.0 | 3.1 | 3.5 | 4.3 | 4.8 | 5.9 | 3.6 | 8.1 |
| Ethylbenzene | 0.2 | — | — | — | — | 0.5 | 0.3 | 0.6 |
| p-Xylene | 1.8 | 1.7 | 1.2 | 2.1 | 2.2 | 3.2 | 1.7 | 4.1 |
| m-Xylene | 4.5 | 3.5 | 3.9 | 4.7 | 4.7 | 7.2 | 3.8 | 8.9 |
| o-Xylene | 1.7 | 0.5 | 0.2 | 0.9 | 1.0 | 2.6 | 1.1 | 3.4 |
| Methylethylbenzene | 0.3 | 0.5 | 0.2 | 1.2 | 0.6 | 1.0 | 1.1 | 0.6 |
| Trimethylbenzene | 5.1 | 1.5 | 6.2 | 6.2 | 4.0 | 6.8 | 3.7 | 9.1 |
| Tetramethylbenzene[A] | 0.6 | — | — | — | — | — | 0.3 | — |
| Time on Stream, hrs.[C] | 12.30 | 22.35 | 42.93 | 26.59 | 28.51 | 14.42 | 17.09 | 18.59 |

[A]Durene was not found in low severity runs. Not all high severity cuts have been analyzed for durene.
[B]Bad gas analyses, C$_5$ + paraffins and naphthenes approach 52% based on obtained results.
[C]Time on stream is to end of cut.
[D]Hot Spot Temperature is the temperature at the hottest spot in the bed.

The data in Table XXVIII demonstrate that there is considerable flexibility in operation conditions and in the products that can be provided by the conversion of methanol with a catalyst comprising an AMS-1B crystalline borosilicate material.

Although a metal-exchanged AMS-1B crystalline borosilicate should be used for the conversion of alcohols to hydrocarbons, it can be pointed out that a nickel-exchanged AMS-1B crystalline borosilicate material is not the only exchanged borosilicate material that can be used. For example, the borosilicate material that is employed in the catalyst can be exchanged with other metal cations, for example, copper, zinc, iron, chromium, etc.

Therefore, in yet another embodiment of the present invention, there is provided a process for the conversion of an alcohol to useful hydrocarbons, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$0.9 \pm 0.2\ M_{2/n}O:B_2O_3:YSiO_2:ZH_2O$, wherein M is at least one cation having a valence of n, Y is within the range of 4 to about 600, and Z is within the range of 0 to about 160.

In addition, there is provided a process for the conversion of an alcohol to hydrocarbon products boiling in the gasoline boiling range or other useful hydrocarbons, which process comprises contacting a feed comprising said alcohol under suitable conversion conditions with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$0.9 \pm 0.2\ M_{2/n}O:B_2O_3:YSiO_2:ZH_2O$, wherein M is at least one cation having a valence of n, Y is within the range of about 4 to about 600, and Z is within the range of 0 to about 160.

Operating conditions for the conversion of an alcohol to useful products boiling within the gasoline boiling range are presented hereinabove.

While conversion of an alcohol in the presence of a catalyst comprising a crystalline borosilicate will result in paraffins, naphthenes, olefins, and aromatics, certain combinations of conditions can be used to maximize a selected product. For example, ranges of values of preferred conditions for several products are summarized hereinbelow in Table XXIX:

TABLE XXIX

| Maximized Product | Preferred Conditions for Selected Maximized Products | | | | |
|---|---|---|---|---|---|
| | Hot Spot Temperature*, | | WHSV | Pressure, | |
| | °F. | °C. | hr$^{-1}$ | Atm | kPa |
| gasoline | 680–820 | 360–438 | 1–8 | 1–5 | 101–507 |
| aromatics | 720–880 | 382–471 | 0.5–6 | 1–10 | 101–1,013 |
| total olefins | 840–1,200 | 449–649 | 0.5–24 | 1–5 | 101–507 |
| ethylene and propylene | 880–1,200 | 471–649 | 0.5–12 | 1–5 | 101–507 |
| isobutylene | 880–1,080 | 471–582 | 3–24 | 1–2 | 101–203 |

*hot spot temperature is the temperature of the hottest spot in the catalyst bed.

Consequently, there is provided a process for the conversion of an alcohol to useful hydrocarbons, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$0.9 \pm 0.2\ M_{2/n}O:B_2O_3:YSiO_2:ZH_2O$, wherein M is at least one cation having a valence of n, Y is within the range of 4 to about 600, and Z is within the range of 0 to about 160.

In one embodiment, there is provided a process for the conversion of an alcohol to hydrocarbon products boiling in the gasoline boiling range, which process comprises contacting a feed comprising said alcohol under suitable conversion conditions with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$0.9 \pm 0.2\ M_{2/n}O:B_2O_3:YSiO_2:ZH_2O$, wherein M is at least one cation having a valence of n, Y is within the range of 4 to about 600, and Z is within the range of 0 to about 160.

Furthermore, there is provided a process for the conversion of an alcohol to aromatics, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M | and having the following composition in terms of mole ratios of oxides:

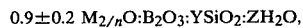
$0.9 \pm 0.2\ M_{2/n}O:B_2O_3:YSiO_2:ZH_2O$, wherein M is at least one cation having a valence of n, Y is within the range of about 4 to about 600, and Z is within the range of 0 to about 160, said conditions comprising a hot spot temperature within the range of about 720° F. (382° C.) to about 880° F. (471° C.), a WHSV within the range of about 0.5 hr$^{-1}$ to about 6 hr$^{-1}$, and a pressure within the range of about 1 atm (101.3 kPa) to about 10 atm (1,013 kPa).

In addition, there is provided a process for the conversion of alcohol to olefins, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M | and having the following composition in terms of mole ratios of oxides:

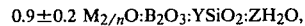
$0.9 \pm 0.2\ M_{2/n}O:B_2O_3:YSiO_2:ZH_2O$, wherein M is at least one cation having a valence of n, Y is within the range of 4 to about 600, and Z is within the range of 0 to about 160, said conditions comprising a hot spot temperature within the range of about 840° F. (449° C.) to about 1,200° F. (649° C.), a WHSV within the range of about 0.5 hr$^{-1}$ to about 24 hr$^{-1}$, and a pressure within the range of about 1 atm (101.3 kPa) to about 5 atm (507 kPa).

As shown in the various examples hereinabove, a catalyst containing an AMS-1B crystalline borosilicate material can be used to catalyze a number of important chemical reactions. These include, but are not limited to, the isomerization of xylenes, the alkylation of benzene with a suitable alkylating agent, and the conversion of an alcohol, such as methanol, to useful products.

Furthermore, a second catalyst can be employed in combination with the principal catalyst containing an AMS-1B crystalline borosilicate material for the conversion of methanol to useful hydrocarbon products. This second catalyst is employed specifically to convert the methanol to dimethyl ether and precedes the principal catalyst which contains the AMS-1B crystalline borosilicate material and which effects the conversion of hydrocarbons other than dimethyl ether. The second catalyst can be incorporated into and can become an integral part of the reactor system that contains the principal catalyst, or it can be used in a distinct and separate reactor unit. The second catalyst is employed in a catalyst bed that is separate from that of the principal catalyst. This second catalyst can be composed of a crystalline AMS-1B borosilicate material, a gamma- or eta-alumina, silica-alumina, boria, boria-alumina, boria-silica, silica-titania, or other similar materials, each of which is used alone or in combination with other materials known to those skilled in the art. The advantage that is provided by the use of this second catalyst which precedes the principal catalyst is the dissipation of the heat of reaction of ether formation in a catalyst bed other than the bed of principal catalyst effecting conversion to hydrocarbons other than dimethyl ether.

What is claimed is:

1. A process for the conversion of an alcohol to useful hydrocarbon products, which process comprises contacting a feed comprising said alcohol under suitable conversion conditions with a catalyst comprising a crystalline borosilicate which comprises a molecular sieve material providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M | and having the following composition in terms of mole ratios of oxides:

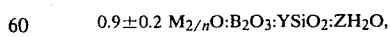
$0.9 \pm 0.2\ M_{2/n}O:B_2O_3:YSiO_2:ZH_2O$, wherein M is at least one cation having a valence of n, Y is between 4 and about 600, and Z is between 0 and about 160.

2. The process of claim 1 wherein said borosilicate provides an X-ray diffraction pattern comprising the following X-ray diffraction lines and assigned strengths:

| d (Å) | Assigned Strength |
|---|---|
| 11.2 ± 0.2 | M-VS |
| 10.0 ± 0.2 | M-MS |
| 5.97 ± 0.07 | W-M |
| 3.82 ± 0.05 | VS |
| 3.70 ± 0.05 | MS |
| 3.62 ± 0.05 | M |
| 2.97 ± 0.02 | W-M |
| 1.99 ± 0.02 | VW-M | after said borosilicate has been calcined at a temperature within the range of about 1,000° F. (538° C.) to about 1,100° F. (593° C.).

3. The process of claim 1, wherein the value of Y for said borosilicate is within the range of about 40 to about 120 and the value of Z for said borosilicate is within the range of 0 to about 40.

4. The process of claim 1, wherein said conditions comprise a hot spot temperature within the range of about 650° F. (343° C.) to about 1,350° F. (732° C.), a pressure within the range of about 0.5 atm (50.7 kPa) to about 30 atm (3,040 kPa), and a WHSV within the range of about 0.1 hr$^{-1}$ to about 50 hr$^{-1}$.

5. The process of claim 2, wherein said conditions comprise a hot spot temperature within the range of about 650° F. (343° C.) to about 1,350° F. (732° C.), a pressure within the range of about 0.5 atm (50.7 kPa) to about 30 atm (3,040 kPa), and a WHSV within the range of about 0.1 hr$^{-1}$ to about 50 hr$^{-1}$.

6. A process for the conversion of an alcohol to hydrocarbon products boiling in the gasoline boiling range, which process comprises contacting a feed comprising said alcohol under suitable conversion conditions with a catalyst comprising a crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

0.9±0.2 M$_{2/n}$O:B$_2$O$_3$:YSiO$_2$:ZH$_2$O, wherein M is at least one cation having a valence of n, Y is within the range of about 4 and about 600, and Z is within the range of 0 to about 160.

7. The process of claim 6 wherein said borosilicate provides an X-ray diffraction pattern comprising the following X-ray diffraction lines and assigned strengths:

| d (Å) | Assigned Strength |
|---|---|
| 11.2 ± 0.2 | M-VS |
| 10.0 ± 0.2 | M-MS |
| 5.97 ± 0.07 | W-M |
| 3.82 ± 0.05 | VS |
| 3.70 ± 0.05 | MS |
| 3.62 ± 0.05 | M |
| 2.97 ± 0.02 | W-M |
| 1.99 ± 0.02 | VW-M | after said borosilicate has been calcined at a temperature within the range of about 1,000° F. (538° C.) to about 1,100° F. (593° C.).

8. The process of claim 6, wherein the value of Y for said borosilicate is within the range of about 40 to about 120 and the value of Z for said borosilicate is within the range of 0 to about 40.

9. The process of claim 6, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

10. The process of claim 7, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

11. The process of claim 8, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

12. The process of claim 10, wherein said borosilicate is a metal-exchanged AMS-1B crystalline borosilicate.

13. The process of claim 12, wherein said borosilicate has been cation-exchanged with nickel.

14. A process for the conversion of an alcohol to hydrocarbon products boiling in the gasoline boiling range, which process comprises contacting a feed comprising said alcohol under suitable conversion conditions with a catalyst comprising a crystalline borosilicate and a porous refractory inorganic oxide, said borosilicate and said inorganic oxide having been intimately admixed with one another, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

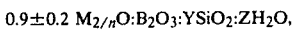

0.9±0.2 M$_{2/n}$O:B$_2$O$_3$:YSiO$_2$:ZH$_2$O, wherein M is at least one cation having a valence of n, Y is within the range of about 4 and about 600, and Z is within the range of 0 to about 160.

15. The process of claim 14, wherein at least one catalytically-active metal is placed onto said borosilicate prior to said borosilicate being mixed with said inorganic oxide.

16. The process of claim 14, wherein said borosilicate provides an X-ray diffraction pattern comprising the following X-ray diffraction lines and assigned strengths:

| d (Å) | Assigned Strength |
|---|---|
| 11.2 ± 0.2 | M-VS |
| 10.0 ± 0.2 | M-MS |
| 5.97 ± 0.07 | W-M |
| 3.82 ± 0.05 | VS |
| 3.70 ± 0.05 | MS |
| 3.62 ± 0.05 | M |
| 2.97 ± 0.02 | W-M |
| 1.99 ± 0.02 | VW-M | after said borosilicate has been calcined at a temperature within the range of about 1,000° F. (538° C.) to about 1,100° F. (593° C.).

17. The process of claim 14, wherein said inorganic oxide of said catalyst is catalytically-active alumina.

18. The process of claim 14, wherein said alcohol is an alcohol containing 1 to 4 carbon atoms.

19. The process of claim 14, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

20. The process of claim 15, wherein said inorganic oxide of said catalyst is catalytically-active alumina.

21. The process of claim 15, wherein said catalytically-active metal is nickel.

22. The process of claim 16, wherein at least one catalytically-active metal is placed onto said borosilicate prior to said borosilicate being mixed with said inorganic oxide.

23. The process of claim 16, wherein said inorganic oxide of said catalyst is catalytically-active alumina.

24. The process of claim 16, wherein said alcohol is an alcohol containing 1 to 4 carbon atoms.

25. The process of claim 16, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

26. The process of claim 21, wherein said inorganic oxide of said catalyst is catalytically-active alumina.

27. The process of claim 21, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

28. The process of claim 22, wherein said inorganic oxide of said catalyst is catalytically-active alumina.

29. The process of claim 22, wherein said catalytically-active metal is nickel.

30. The process of claim 26, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

31. The process of claim 29, wherein said inorganic oxide of said catalyst is catalytically-active alumina.

32. The process of claim 29, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

33. The process of claim 30, wherein said alcohol is an alcohol containing 1 to 4 carbon atoms.

34. The process of claim 31, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

35. The process of claim 34, wherein said alcohol is an alcohol containing 1 to 4 carbon atoms.

36. The process of claim 34, wherein said alcohol is a monohydric alcohol containing 1 to 4 carbon atoms.

37. The process of claim 36, wherein said alcohol is methanol.

38. The process of claim 37, wherein said conditions comprise a hot spot temperature within the range of about 680° F. (360° C.) to about 820° F. (438° C.), a pressure within the range of about 1 atm (101.3 kPa) to about 5 atm (506.5 kPa), and a WHSV within the range of about 1 hr$^{-1}$ to about 8 hr$^{-1}$.

39. A process for the conversion of an alcohol to olefins, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

0.9±0.2 M$_{2/n}$O:B$_2$O$_3$:YSiO$_2$:ZH$_2$O, wherein M is at least one cation having a valence of n, Y is within the range of 4 to about 600, and Z is within the range of 0 to about 160, said conditions comprising a hot spot temperature within the range of about 840° F. (449° C.) to about 1,200° F. (649° C.), a WHSV within the range of about 0.5 hr$^{-1}$ to about 24 hr$^{-1}$, and a pressure within the range of about 1 atm (101.3 kPa) to about 5 atm (506.5 kPa).

40. The process of claim 39, wherein said borosilicate provides an X-ray diffraction pattern comprising the following X-ray diffraction lines and assigned strengths:

| d (Å) | Assigned Strength |
|---|---|
| 11.2 ± 0.2 | M–VS |
| 10.0 ± 0.2 | M–MS |
| 5.97 ± 0.07 | W–M |
| 3.82 ± 0.05 | VS |
| 3.70 ± 0.05 | MS |
| 3.62 ± 0.05 | M |
| 2.97 ± 0.02 | W–M |
| 1.99 ± 0.02 | VW–M | after said borosilicate has been calcined at a temperature within the range of about 1,000° F. (538° C.) to about 1,100° F. (593° C.).

41. The process of claim 39, wherein the value of Y for said borosilicate is within the range of about 40 to about 120 and the value of Z for said borosilicate is within the range of 0 to about 40.

42. The process of claim 40, wherein nickel is the metal that has been cation-exchanged into said borosilicate.

43. The process of claim 42, wherein said catalyst comprises further a refractory inorganic oxide.

44. The process of claim 43, wherein said refractory inorganic oxide of said catalyst is catalytically-active alumina.

45. A process for the conversion of an alcohol to aromatics, which process comprises contacting a feed comprising said alcohol under suitable conversion conditions with a catalyst comprising a metal-exchanged crystalline borosilicate, said borosilicate comprising a molecular sieve material providing an X-ray diffraction pattern comprising the following X-ray diffraction lines and assigned strengths:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |

-continued

| d (Å) | Assigned Strength |
|---|---|
| 1.99 ± 0.02 | VW–M | and having the following composition in terms of mole ratios of oxides:

$$0.9 \pm 0.2 \; M_{2/n}O:B_2O_3:YSiO_2:ZH_2O,$$

wherein M is at least one cation having a valence of n, Y is within the range of 4 to about 600, and Z is within the range of 0 to about 160, said conditions comprising a hot spot temperature within the range of about 720° F. (382° C.) to about 880° F. (471° C.), a WHSV within the range of about 0.5 $hr^{-1}$ to about 6 $hr^{-1}$, and a pressure within the range of about 1 atm (101.3 kPa) to about 10 atm (1,013 kPa).

46. The process of claim 45, wherein said borosilicate provides an X-ray diffraction pattern comprising the following X-ray diffraction lines and assigned strengths:

| d (Å) | Assigned Strength |
|---|---|
| 11.2 ± 0.2 | M–VS |
| 10.0 ± 0.2 | M–MS |
| 5.97 ± 0.07 | W–M |
| 3.82 ± 0.05 | VS |
| 3.70 ± 0.05 | MS |
| 3.62 ± 0.05 | M |
| 2.97 ± 0.02 | W–M |
| 1.99 ± 0.02 | VW–M | after said borosilicate has been calcined at a temperature within the range of about 1,000° F. (538° C.) to about 1,100° F. (593° C.).

47. The process of claim 45, wherein the value of Y for said borosilicate is within the range of about 40 to about 120 and the value of Z for said borosilicate is within the range of 0 to about 40.

48. The process of claim 46, wherein nickel is the metal that has been cation-exchanged into said borosilicate.

49. The process of claim 48, wherein said catalyst further comprises a refractory inorganic oxide.

50. The process of claim 49, wherein said refractory inorganic oxide of said catalyst is a catalytically-active alumina.

* * * * *

UNITED STATES PATENT OFFICE
CERTIFICATE OF CORRECTION

Patent No. 4,292,458  Dated September 29, 1981

Inventor(s) Marvin R. Klotz

It is certified that error appears in the above-identified patent and that said Letters Patent are hereby corrected as shown below:

| | |
|---|---|
| Column 2, line 21, | "are" should be -- is --. |
| Column 7, line 53, | "Assigned Strength" should be over column containing "VW". |
| Column 11, line 18, | "absorption" should be -- adsorption --. |
| Column 13, line 12, | "WHSV's" should be --WHSV--. |
| Column 22, lines 29-30, | "Z-H$_2$O," should be -- ZH$_2$O, -- on one line. |
| Column 22, lines 41-42, | "Z-H$_2$O," should be -- ZH$_2$O, -- on one line. |
| Column 25, line 66, | "(329°F.) 165°C. should be -- 329°F. (165°C.) --. |
| Column 26, lines 19-20, | "Ni(-NO$_3$)$_2$.6H$_2$O" should be -- Ni(NO$_3$)$_2$.6H$_2$O --. |
| Column 26, line 63, | "lightend" should be -- light-end --. |
| Column 28, line 28, | "(I/I$_o$)" should be -- (I/Io) --. |
| Column 33, line 16, | "preformed" should be -- performed --. |
| Column 44, | For Cut No. 3A, in Table XXVIII, the value of Tetramethylbenzene should be -- 0.3 --. |

UNITED STATES PATENT OFFICE
CERTIFICATE OF CORRECTION

Patent No. 4,292,458     Dated September 29, 1981

Inventor(s) Marvin R. Klotz

It is certified that error appears in the above-identified patent and that said Letters Patent are hereby corrected as shown below:

Column 44,     For Cut No. 3B in Table XXVIII, change the value of Tetramethylbenzene from "0.3" to -- - --.

Column 48, line 18,     "of" should be -- to --.

Signed and Sealed this

Tenth Day of August 1982

[SEAL]

Attest:

Attesting Officer

GERALD J. MOSSINGHOFF

Commissioner of Patents and Trademarks